(12) United States Patent
Kurzrock et al.

(10) Patent No.: US 7,968,115 B2
(45) Date of Patent: Jun. 28, 2011

(54) LIPOSOMAL CURCUMIN FOR TREATMENT OF CANCER

(75) Inventors: Razelle Kurzrock, Houston, TX (US); Lan Li, Houston, TX (US); Kapil Mehta, Houston, TX (US); Bharat Bhushan Aggarawal, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 1275 days.

(21) Appl. No.: 11/221,179

(22) Filed: Sep. 7, 2005

(65) Prior Publication Data

US 2006/0067998 A1      Mar. 30, 2006

(51) Int. Cl.
*A61K 9/127*   (2006.01)
(52) U.S. Cl. ............................................... 424/450
(58) Field of Classification Search .............. 424/450
See application file for complete search history.

(56) References Cited

U.S. PATENT DOCUMENTS

| | | | |
|---|---|---|---|
| 5,858,397 A | 1/1999 | Lim et al. | |
| 6,126,966 A | 10/2000 | Abra et al. | |
| 6,664,272 B2 * | 12/2003 | Snyder et al. | 514/327 |
| 6,673,843 B2 * | 1/2004 | Arbiser | 514/679 |
| 2001/0051184 A1 * | 12/2001 | Heng | 424/461 |
| 2003/0118636 A1 * | 6/2003 | Friesen et al. | 424/450 |
| 2004/0224012 A1 * | 11/2004 | Suvanprakorn et al. | 424/450 |
| 2005/0048109 A1 * | 3/2005 | Albrecht et al. | 424/450 |
| 2005/0181036 A1 * | 8/2005 | Aggarwal et al. | 424/450 |
| 2006/0229239 A9 | 10/2006 | Shoji et al. | |

OTHER PUBLICATIONS

Voskoglou-Nomikos et al in Clinical Cancer Research, vol. 9, Sep. 2003, pp. 4227-4239.*

* cited by examiner

*Primary Examiner* — Gollamudi S Kishore
(74) *Attorney, Agent, or Firm* — Chalker Flores, LLP; Edwin S. Flores; Daniel J. Chalker

(57) ABSTRACT

The present invention provides a compositions and methods for the treatment of cancer, including pancreatic cancer, breast cancer and melanoma, in a human patient. The methods and compositions of the present invention employ curcumin or a curcumin analogue encapsulated in a colloidal drug delivery system, preferably a liposomal drug delivery system. Suitable colloidal drug delivery systems also include nanoparticles, nanocapsules, microparticles or block copolymer micelles. The colloidal drug delivery system encapsulating curcumin or a curcumin analogue is administered parenterally in a pharmaceutically acceptable carrier.

3 Claims, 18 Drawing Sheets

MTT Proliferation/Survival Assays

Bxpc-3

Capan-1

Apoptosis Assay (Annexin-V/PI)

Bxpc-3

HS766-T

LIPOSOMAL CURCUMIN FOR TREATMENT OF CANCER

FIELD OF THE INVENTION

The invention relates generally to the field of cancer therapeutics. More specifically, the invention relates to the use of curcumin or curcumin analogues to treat cancers, including pancreatic cancers.

BACKGROUND OF THE INVENTION

Curcumin (diferuloyl methane) is a natural dietary ingredient, which has been found to have antioxidant and anti-inflammatory properties. Curcumin is found in significant amounts in turmeric, a spice derived from the perennial herb *Curcuma longa* L. It can suppress the growth of certain cancers in the laboratory and prevent the appearance of cancers in animal studies, however the effects of curcumin and curcumin analogues on cancer cells are highly variable, depending on the type of cancer studied. The use of curcumin in the treatment of pancreatic cancer in vivo, for example, has not, been previously studied.

Pancreatic cancer is a lethal disease for which there is currently no adequate treatment. The majority of the 30,000 new cases of pancreatic cancer diagnosed yearly in the United States are non-resectable due to locally advanced or metastatic disease. Five-year survival of newly-diagnosed pancreatic cancer patients is less than 5%. Gemcitabine, which is considered the most effective chemotherapeutic agent available, results in responses in about 5% of patients, and survival benefit is minimal. These observations suggest that new approaches for the management of this malignancy are urgently needed.

Curcumin and some curcumin derivatives have been previously identified as having antioxidant, anti-inflammatory, and in some contexts, antitumor activity when studied in vitro. (Araujo and Leon, 2001). However the antitumor effects are highly unpredictable. For example, Khar et al. found that curcumin induced apoptosis in leukemia, breast, colon, hepatocellular and ovarian carcinoma cell lines in vitro, but failed to evidence cytotoxic effects in lung, kidney, prostate, cervix, CNS malignancy and melanoma cell lines (Khar et al., 2001). In one instance, an in vivo model of human breast cancer showed that curcumin actually inhibited chemotherapy-induced apoptosis of the cancer cells being studied (Somasundaram et al., 2002). The effects of curcumin on cancer cells appears therefore to be variable depending on the specific type of cancer cell treated.

Oral and topical administration of curcumin has been previously studied. Even at high oral doses, curcumin shows little in the way of toxicity in animal studies. Studies in rats where the animals were given 1 to 5 g/kg of curcumin found that 75% of the curcumin was excreted in the feces and only traces appeared in the urine. (Araujo and Leon, 2001). However despite its low toxicity, curcumin's bioavailability after oral administration is poor and in vivo concentrations of curcumin that are growth inhibitory to tumor cells in vitro cannot be achieved by the oral route. Intravenous administration of free curcumin has also been found to be ineffective to achieve significant concentrations of curcumin in any tissue, since curcumin appears to be rapidly metabolized in circulation.

Curcumin has been the subject of several clinical trials in human patients, but has only been found to have limited utility in the prevention, and possibly the treatment, of certain cancers of the gastrointestinal tract. Due to the rapid metabolism of curcumin when administered orally or intravenously, curcumin therefore has never been shown to be an effective potential preventative or treatment for cancers other than those of the gastrointestinal tract or cancers where topical application of curcumin would be appropriate. It would therefore be desirable to identify additional cancers that can be effectively treated with curcumin and curcumin analogues, and to develop routes of in vivo administration of the drug capable of producing concentrations that are inhibitory to tumor cell growth.

Thus, there remains a need in the art for an effective treatment of carcinomas in vivo by curcumin or curcumin analogues. Also, there remains a need for a more effective means of delivering curcumin or curcumin analogues to carcinomas than can be provided through oral or topical delivery.

SUMMARY OF THE INVENTION

The present invention provides methods for the treatment or prevention of cancer in a human patient or other mammalian subject (i.e. any mammalian animal) comprising the steps of (a) formulating a colloidal drug delivery system encapsulating curcumin or a curcumin analogue as the active ingredient and (b) delivering the active ingredient to cancer cells in the patient by parenteral administration of the colloidal drug delivery system in a pharmaceutically acceptable carrier. Cancers that may be treated or prevented using the present invention include, but are not limited to, pancreatic cancer, breast cancer and melanoma. Appropriate colloidal drug delivery systems include, but are not limited to, both lipid-based and polymer-based colloidal drug delivery systems such as liposomes, nanoparticles, microparticles or block copolymer micelles.

The invention also provides methods for the treatment or prevention of cancer, including pancreatic cancer, breast cancer and melanoma, in a human patient or other mammalian subject, comprising the steps of (a) formulating a polymeric, non-colloidal drug delivery system encapsulating curcumin or a curcumin analogue as the active ingredient and (b) delivering the active ingredient to cancer cells in the patient by parenteral administration of the polymeric drug delivery system in a pharmaceutically acceptable carrier. Appropriate polymeric non-colloidal drug delivery systems include, but are not limited to, hydrogels and films.

The present invention also provides compositions for the treatment or prevention of cancer, including pancreatic cancer, breast cancer and melanoma comprising curcumin or a curcumin analogue encapsulated in a colloidal drug delivery system. Appropriate colloidal drug delivery systems include, but are not limited to, both lipid-based and polymer-based colloidal drug delivery systems such as liposomes, nanoparticles, microparticles or block copolymer micelles.

The invention further provides compositions for the treatment or prevention of cancer, including pancreatic cancer, breast cancer and melanoma, comprising curcumin or a curcumin analogue encapsulated in a non-colloidal polymeric drug delivery system. Appropriate polymeric non-colloidal drug delivery systems include, but are not limited to, hydrogels and films.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION

Figure 1:
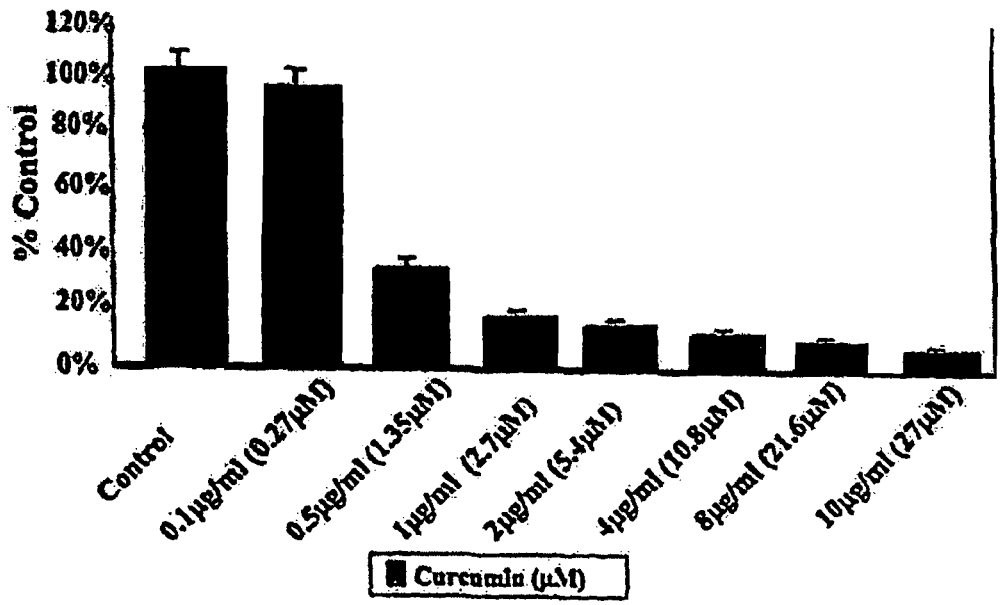
FIG. 1 MTT proliferation/survival assay of Bxpc-3 pancreatic cells.
Figure 2:
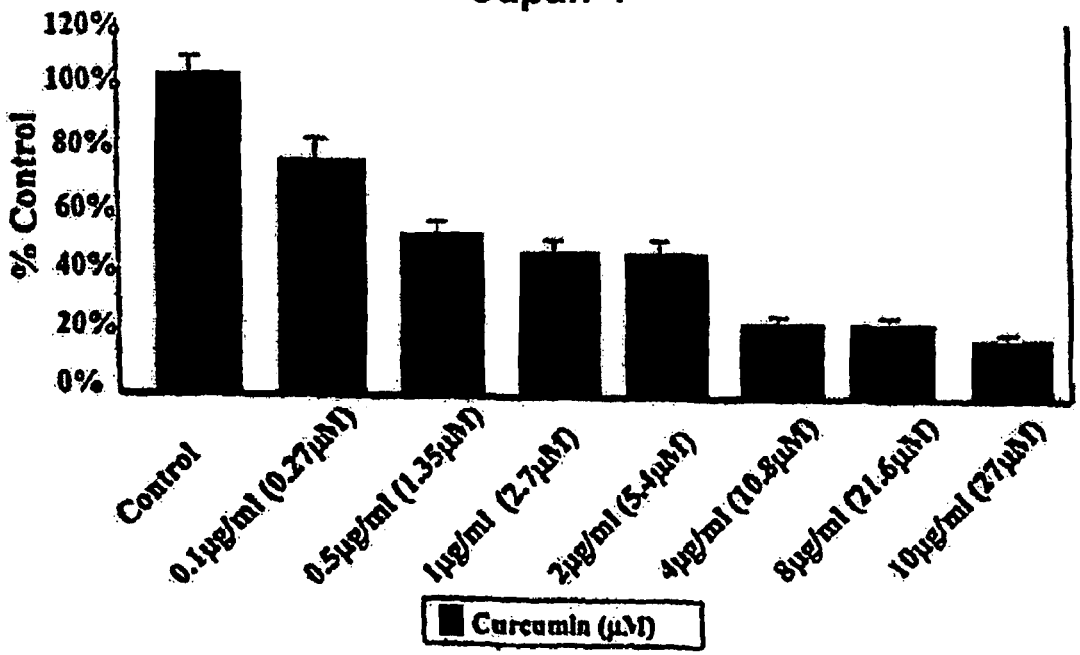
FIG. 2 MTT proliferation/survival assay of Capan-1 pancreatic cells.
Figure 3:
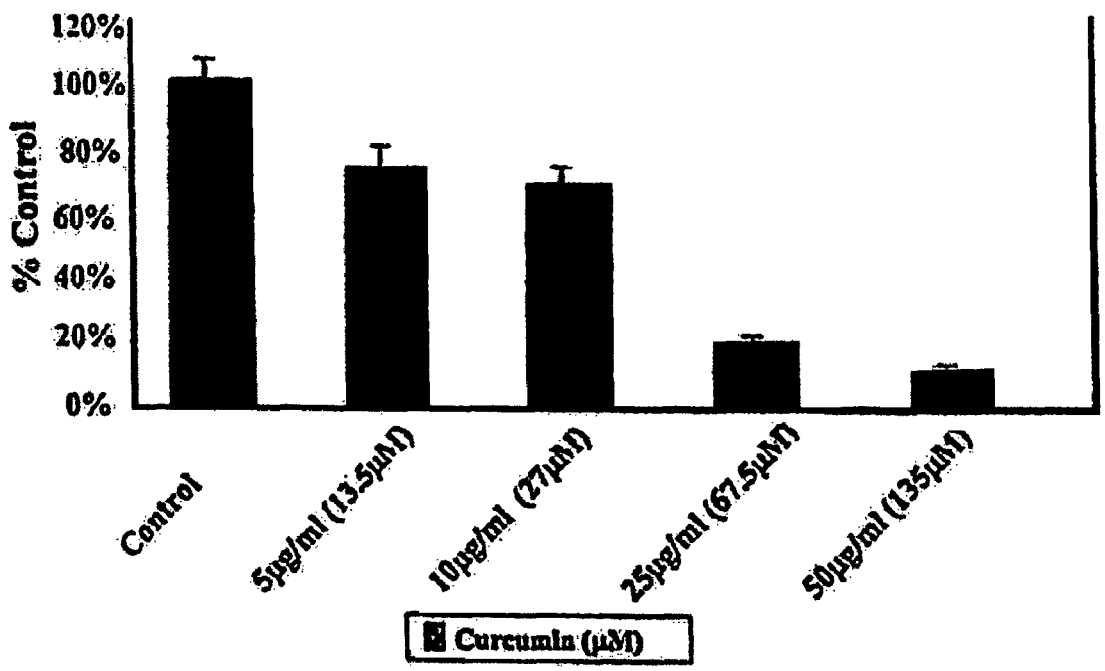
FIG. 3 MTT proliferation/survival assay of Capan-2 pancreatic cells.
Figure 4:
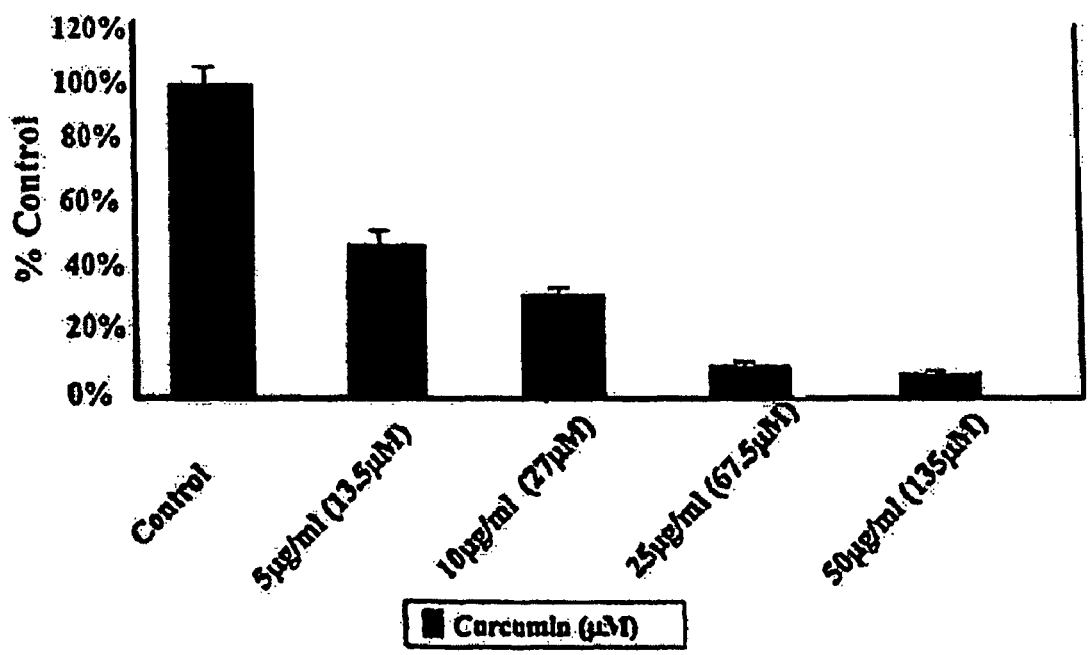
FIG. 4 MTT proliferation/survival assay of HS766-T pancreatic cells.
Figure 5:
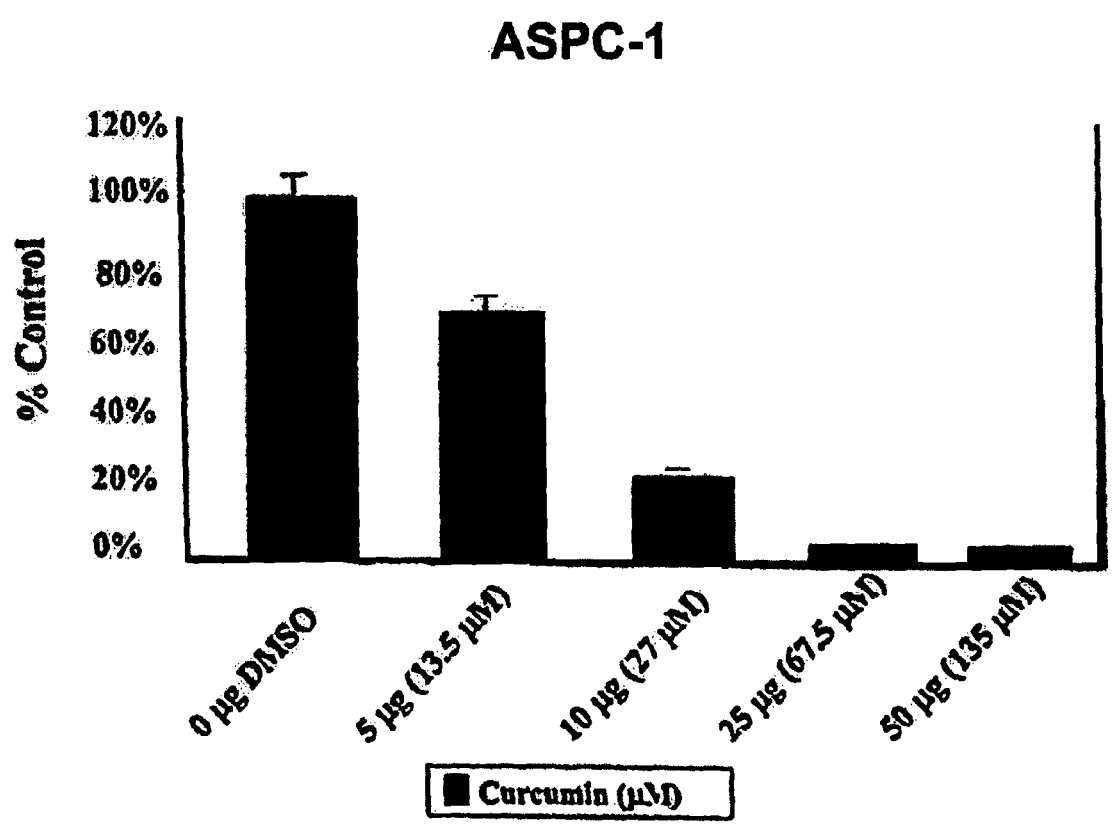
FIG. 5 MTT proliferation/survival assay of ASPC-1 pancreatic cells.
Figure 6:
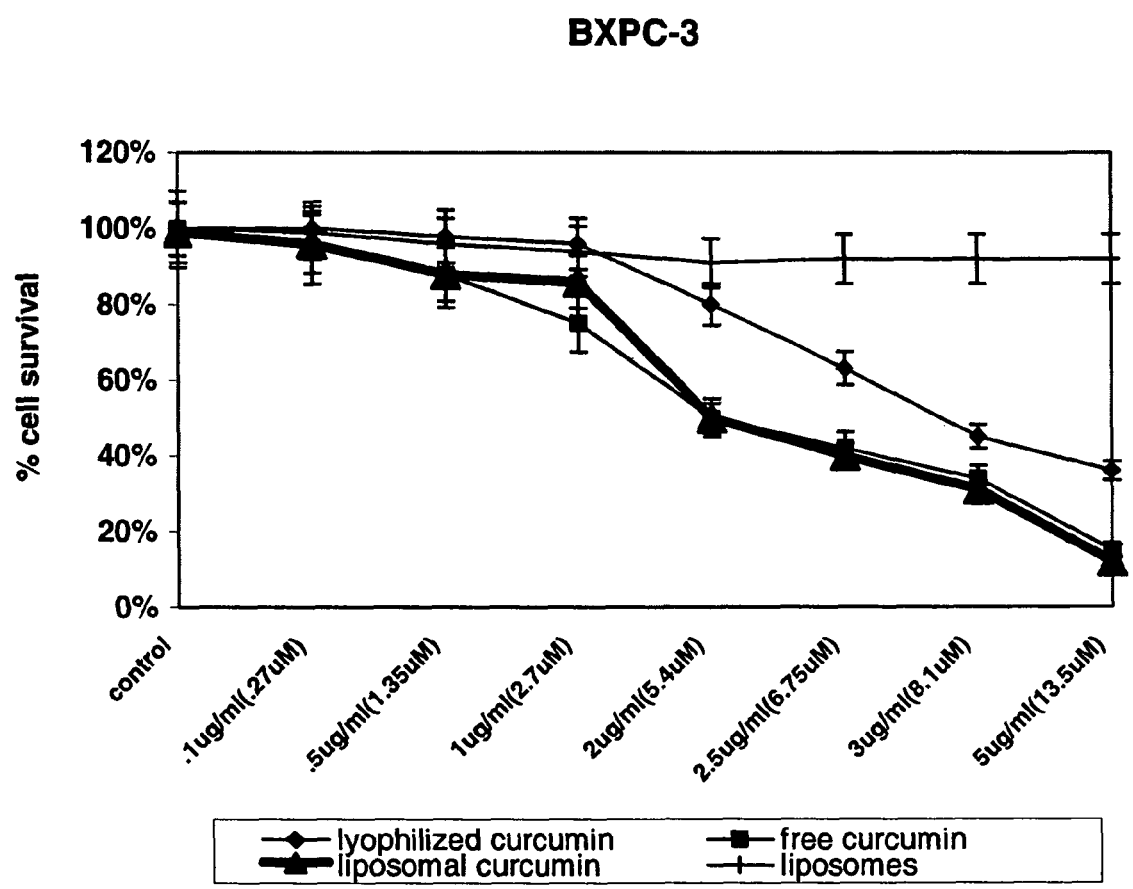
FIG. 6 MTT proliferation/survival assay results for BxPC-3 pancreatic cells.
Figure 7:
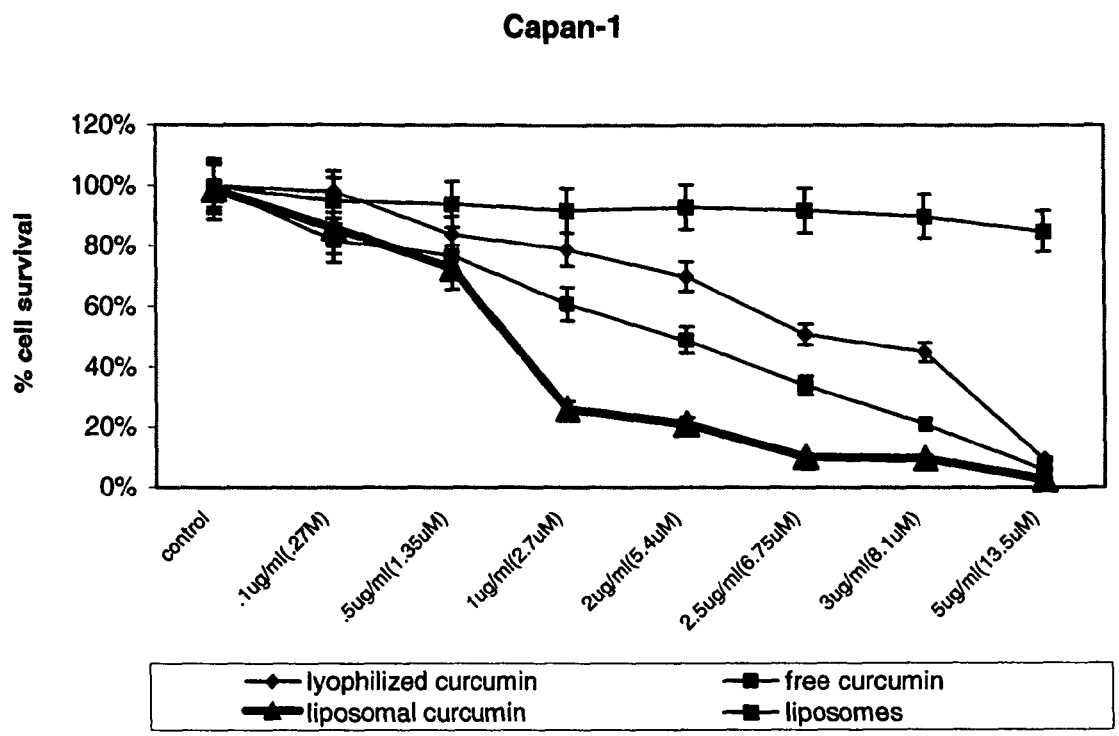
FIG. 7 MTT proliferation/survival assay results for Capan-1 pancreatic cells.
Figure 8:
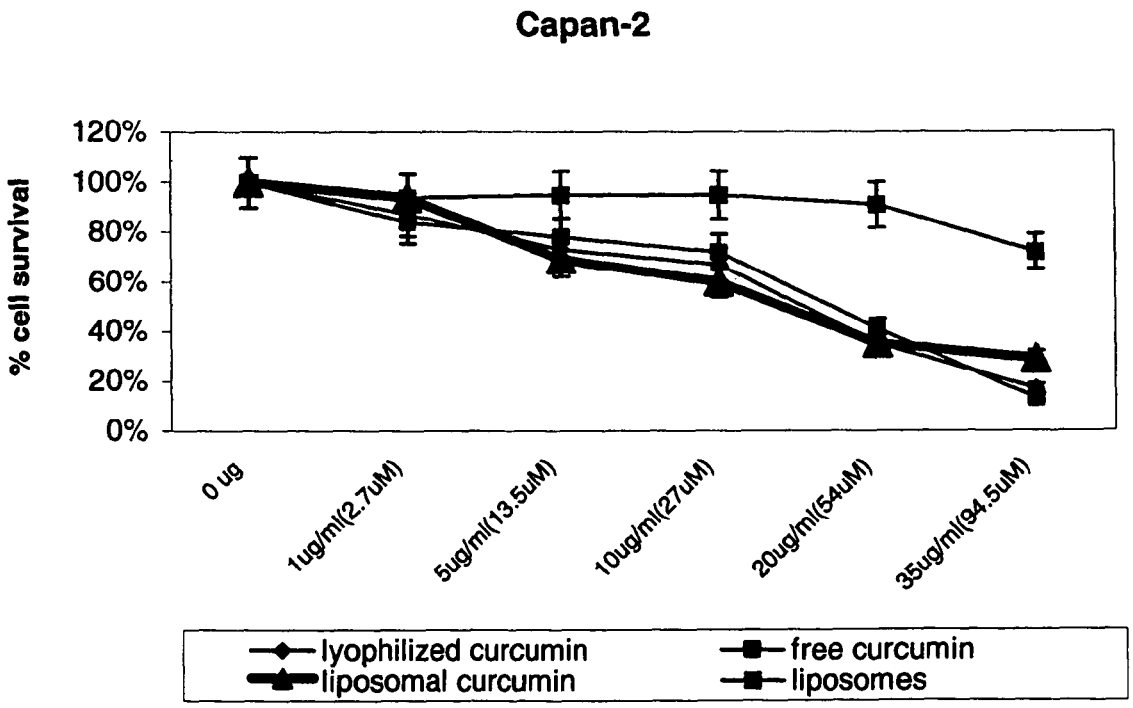
FIG. 8 MTT proliferation/survival assay results for Capan-2 pancreatic cells.
Figure 9:
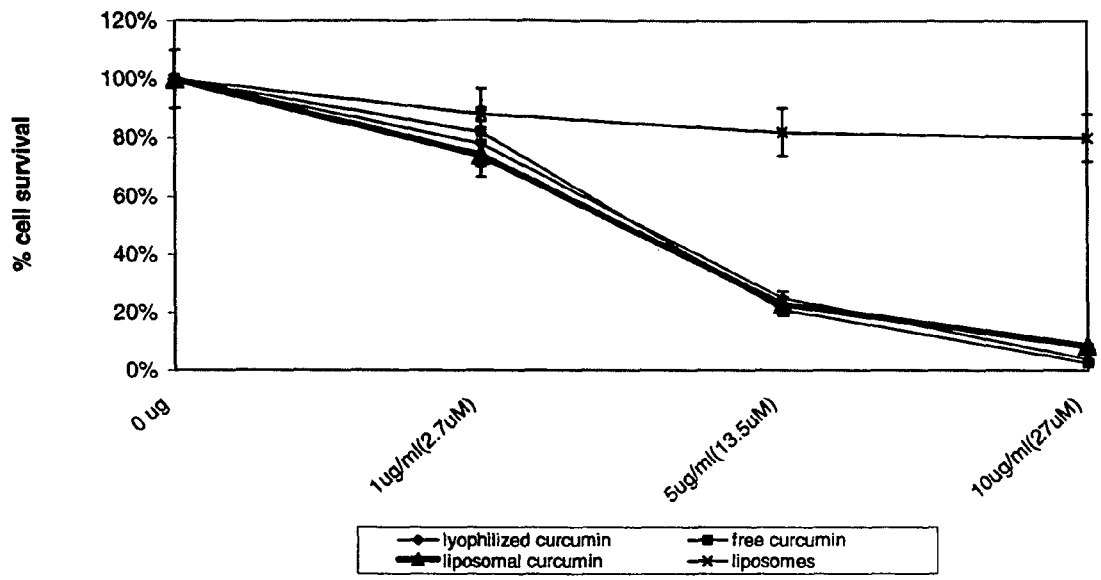
FIG. 9 MTT proliferation/survival assay results for HS766-T pancreatic cells.
Figure 10:
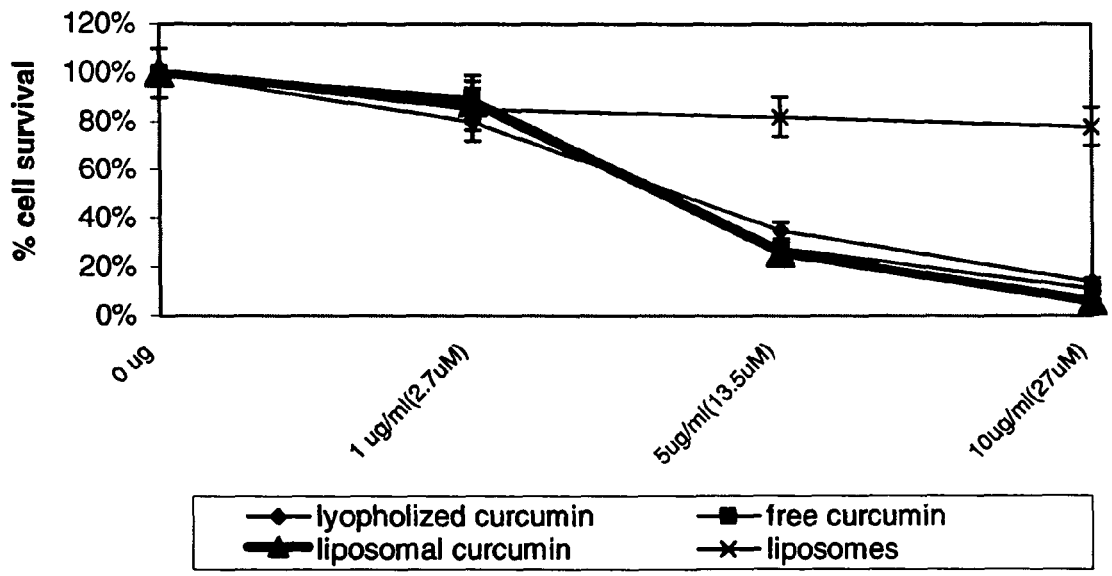
FIG. 10 MTT proliferation/survival assay results for ASPC-1 pancreatic cells.

The present invention provides compositions and methods useful for the treatment of cancer in which curcumin, or a curcumin analogue having antitumor activity, is administered parenterally to a patient using a colloidal drug-delivery system. In certain embodiments, the colloidal drug-delivery system used is a liposomal drug delivery system. In other embodiments, the colloidal-drug-delivery system used are composed of microparticles (or microspheres), nanoparticles (or nanospheres), nanocapsules, block copolymer micelles, or other polymeric drug delivery systems. In further embodiments, the drug delivery system used is a polymer-based, non-colloidal drug delivery system such as hydrogels, films or other types of polymeric drug delivery system. In yet further embodiments, the curcumin, curcumin analogues or curcumin metabolites may be parenterally administered in a lipid-based solvent.

The invention provides compositions and methods useful for treatment or prevention of cancers of any of a wide variety of types, including both solid tumors and non-solid tumors such as leukemia and lymphoma. In certain embodiments, the cancer treated is pancreatic cancer. The present invention can be used to treat either malignant or benign cancers. Carcinomas, sarcomas, myelomas, lymphomas, and leukemias can all be treated using the present invention, including those cancers which have a mixed type. Specific types of cancer that can also be treated include, but are not limited to: adenocarcinoma of the breast or prostate; all forms of bronchogenic carcinoma of the lung; myeloid; melanoma; hepatoma; neuroblastoma; papilloma; apudoma; choristoma; branchioma; malignant carcinoid syndrome; carcinoid heart disease; carcinoma (e.g., Walker, basal cell, basosquamous, Brown-Pearce, ductal, Ehrlich tumor, in situ, Krebs 2, merkel cell, mucinous, non-small cell lung, oat cell, papillary, scirrhous, bronchiolar, bronchogenic, squamous cell, and transitional cell), histiocytic disorders; leukemia (e.g., B-cell, mixed-cell, null-cell, T-cell, T-cell chronic, HTLV-II-associated, lyphocytic acute, lymphocytic chronic, mast-cell, and myeloid); histiocytosis malignant; Hodgkin's disease; immunoproliferative small; non-Hodgkin's lymphoma; plasmacytoma; reticuloendotheliosis; melanoma; chondroblastoma; chondroma; chondrosarcoma; fibroma; fibrosarcoma; giant cell tumors; histiocytoma; lipoma; liposarcoma; mesothelioma; myxoma; myxosarcoma; osteoma; osteosarcoma; Ewing's sarcoma; synovioma; adenofibroma; adenolymphoma; carcinosarcoma; chordoma; craniopharyngioma; dysgermiinoma; hamartoma; mesenchymoma; mesonephroma; myosarcoma; ameloblastoma; cementoma; odontoma; teratoma; thymoma; trophoblastic tumor; adenocarcinoma; adenoma; cholangioma; cholesteatoma; cylindroma; cystadenocarcinoma; cystadenoma; granulosa cell tumor; gynandroblastoma; hepatoma; hidradenoma; islet cell tumor; leydig cell tumor; papilloma; sertoli cell tumor; theca cell tumor; leiomyoma; leiomyosarcoma; myoblastoma; myoma; myosarcoma; rhabdomyoma; rhabdomyosarcoma; ependymoma; ganglioneuroma; glioma; medulloblastoma; meningioma; neurilemmoma; neuroblastoma; neuroepithelioma; neurofibroma; neuroma; paraganglioma; paraganglioma nonchromaffin; angiokeratoma; angiolymphoid hyperplasia with eosinophilia; angioma sclerosing; angiomatosis; glomangioma; hemangioendothelioma; hemangioma; hemangiopericytoma; hemangiosarcoma; lymphangioma; lymphangiomyoma; lymphangiosarcoma; pinealoma; carcinosarcoma; chondrosarcoma; cystosarcoma phyllodes; fibrosarcoma; hemangiosarcoma; leiomyosarcoma; leukosarcoma; liposarcoma; lymphangiosarcoma; myosarcoma; myxosarcoma; ovarian carcinoma; rhabdomyosarcoma; sarcoma (e.g., Ewing's, experimental, Kaposi's, and mast-cell); neoplasms (e.g., bone, breast, digestive system, colorectal, liver, pancreatic, pituitary, testicular, orbital, head and neck, central nervous system, acoustic, pelvic, respiratory tract, and urogenital); neurofibromatosis, and cervical dysplasia), and the like.

The methods of the present invention are useful for the treatment or prevention of cancer in all mammalian subjects, including particularly human patients. As used herein, a patient is a human patient. Also as used herein, treatment means any amelioration of the cancer Methods of treatment, as used herein, means the use of compositions or medicaments to treat patients and other mammalian subjects having cancer in order to at least ameliorate the symptoms of cancer or to halt, inhibit or reverse the progress of the disease. Methods of prevention, as used herein, means to treat patients prophylactically to prevent or inhibit onset of cancer in patients or mammalian subjects who have a susceptibility to developing the disease.

I. Curcumin and Curcumin Analogues

As used herein curcumin is also known as diferuloylmethane or (E,E)-1,7-bis(4-hydroxy-3-methoxyphenyl)-1,6-heptadiene-3,5,-dione and has the chemical structure depicted below:

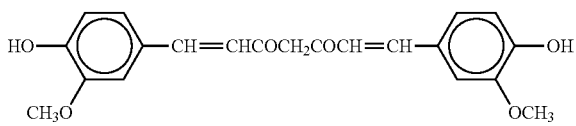

Curcumin may be derived from a natural source, the perennial herb *Curcuma longa* L., which is a member of the Zingiberaceae family. The spice turmeric is extracted from the rhizomes of *Curcuma longa* L. and has long been associated with traditional-medicine treatments used in Hindu and Chinese medicine. Turmeric was administered orally or topically in these traditional treatment methods.

Curcumin is soluble in ethanol, alkalis, ketones, acetic acid and chloroform. It is insoluble in water. Curcumin is therefore lipophilic, and generally readily associates with lipids, e.g. many of those used in the colloidal drug-delivery systems of the present invention. In certain embodiments, curcumin can also be formulated as a metal chelate.

As used herein, curcumin analogues are those compounds which due to their structural similarity to curcumin, exhibit anti-proliferative or pro-apoptotic effects on cancer cells similar to that of curcumin. Curcumin analogues which may have anti-cancer effects similar to curcumin include Ar-tumerone, methylcurcumin, demethoxy curcumin, bis-demethoxycurcumin, sodium curcuminate, dibenzoylmethane, acetylcurcumin, feruloyl methane, tetrahydrocurcumin, 1,7-bis(4-hydroxy-3-methoxyphenyl)-1,6-heptadiene-3,5-dione (curcumin1), 1,7-bis(piperonyl)-1,6-heptadiene-3,5-dione(piperonyl curcumin) 1,7-bis(2-hydroxy naphthyl)-1,6-heptadiene-2,5-dione(2-hydroxyl naphthyl curcumin), 1,1-bis(phenyl)-1,3,8,10-undecatetraene-5,7-dione (cinnamyl curcumin) and the like (Araujo and Leon, 2001; Lin et al., 2001; John et al., 2002; see also Ishida et al., 2002). Curcumin analogues may also include isomers of curcumin, such as the (Z,E) and (Z,Z) isomers of curcumin. In a related embodiment, curcumin metabolites which have anti-cancer effects similar to curcumin can also be used in the present invention. Known curcumin metabolites include glucoronides of tetrahydrocurcumin and hexahydrocurcumin, and dihydroferulic acid. In certain embodiments, curcumin analogues or metabolites can be formulated as metal chelates, especially copper chelates. Other appropriate derivatives of curcumin, curcumin analogues and curcumin metabolites appropriate for use in the present invention will be apparent to one of skill in the art.

As used herein, "active ingredient" refers to curcumin, or a curcumin analogue or metabolite which exhibits anti-cancer activity when administered to a cancer patient.

II. Liposomes and Other Colloidal Drug Delivery Vehicles

Colloidal drug delivery vehicles including liposomes can be used in the present invention to deliver curcumin or curcumin analogues or metabolites to cancer cells in a patient. Curcumin or a curcumin analogue or metabolite is encapsulated in a colloidal drug delivery vehicle that is capable of delivering the drug to target cancer cells. Whenever "encapsulation" is used in this patent it is meant to include incorporation as well.

As used herein, a colloidal drug delivery vehicle is one that comprises particles that are capable of being suspended in a pharmaceutically acceptable liquid medium wherein the size range of the particles ranges from several nanometers to several micrometers in diameter. The colloidal drug delivery systems contemplated by the present invention particularly include those that substantially retain their colloidal nature when administered in vivo. Colloidal drug delivery systems include, but are not limited to, lipid-based and polymer-based particles. Examples of colloidal drug delivery systems include liposomes, nanoparticles, (or nanospheres), nanocapsules, microparticles (or microspheres), and block copolymer micelles.

Liposomes bear many resemblances to cellular membranes and are contemplated for use in connection with the present invention as carriers for curcumin, curcumin analogues, curcumin metabolites, or derivatives of curcumin, curcumin analogues or curcumin metabolites. They are widely suitable as both water- and lipid-soluble substances can be encapsulated, i.e., in the aqueous spaces and within the bilayer itself, respectively. The liposomal formulation of the liposome can be modified by those of skill in the art to maximize the solubility of curcumin or a curcumin analogue or metabolite based on their hydrophobicity. Curcumin, for example, is a water insoluble compound that is soluble in ethanol, ketone, and chloroform and therefore would be expected to be relatively lipophilic. It is also possible to employ liposomes for site-specific delivery of the active ingredient by selectively modifying the liposomal formulation.

III. Lipid Composition of Liposomes

Liposomes suitable for use in the delivery of curcumin or curcumin analogues or metabolites include those composed primarily of vesicle-forming lipids. Appropriate vesicle-forming lipids for use in the present invention include those lipids which can form spontaneously into bilayer vesicles in water, as exemplified by the phospholipids.

Selection of the appropriate lipids for liposome composition is governed by the factors of: (1) liposome stability, (2) phase transition temperature, (3) charge, (4) non-toxicity to mammalian systems, (5) encapsulation efficiency, (6) lipid mixture characteristics. It is expected that one of skill in the art who has the benefit of this disclosure could formulate liposomes according to the present invention which would optimize these factors. The vesicle-forming lipids of this type are preferably ones having two hydrocarbon chains, typically acyl chains, and a head group, either polar or nonpolar. The hydrocarbon chains may be saturated or have varying degrees of unsaturation. There are a variety of synthetic vesicle-forming lipids and naturally-occurring vesicle-forming lipids, including the sphingolipids, ether lipids, sterols, phospholipids, particularly the phosphoglycerides, and the glycolipids, such as the cerebrosides and gangliosides.

Phosphoglycerides include phospholipids such as phosphatidylcholine, phosphatidylethanolamine, phosphatidic acid, phosphatidylinositol, phosphatidylserine phosphatidylglycerol and diphosphatidylglycerol (cardiolipin), where the two hydrocarbon chains are typically between about 14-22 carbon atoms in length, and have varying degrees of unsaturation. As used herein, the abbreviation "PC" stands for phosphatidylcholine, and "PS" stand for phosphatidylserine. Lipids containing either saturated and unsaturated fatty acids are widely available to those of skill in the art. Additionally, the two hydrocarbon chains of the lipid may be symmetrical or asymmetrical. The above-described lipids and phospholipids whose acyl chains have varying lengths and degrees of saturation can be obtained commercially or prepared according to published methods.

Exemplary phosphatidylcholines include dilauroyl phophatidylcholine, dimyristoylphophatidylcholine, dipalmitoylphophatidylcholine, distearoylphophatidylcholine, diarachidoylphophatidylcholine, dioleoylphophatidylcholine, dilinoleoyl-phophatidylcholine, dierucoylphophatidylcholine, palmitoyl-oleoyl-phophatidylcholine, egg phosphatidylcholine, myristoyl-palmitoylphosphatidylcholine, palmitoyl-myristoyl-phosphatidylcholine, myristoyl-stearoylphosphatidylcholine, palmitoyl-stearoyl-phosphatidylcholine, stearoyl-palmitoylphosphatidylcholine, stearoyl-oleoyl-phosphatidylcholine, stearoyl-linoleoylphosphatidylcholine and palmitoyl-linoleoyl-phosphatidylcholine. Assymetric phosphatidylcholines are referred to as 1-acyl, 2-acyl-sn-glycero-3-phosphocholines, wherein the acyl groups are different from each other. Symmetric phosphatidylcholines are referred to as 1,2-diacyl-sn-glycero-3-phosphocholines. As used herein, the abbreviation "PC" refers to phosphatidylcholine. The phosphatidylcholine 1,2-dimyristoyl-sn-glycero-3-phosphocholine is abbreviated herein as "DMPC." The phosphatidylcholine 1,2-dioleoyl-sn-glycero-3-phosphocholine is abbreviated herein as "DOPC." The phosphatidylcholine 1,2-dipalmitoyl-sn-glycero-3-phosphocholine is abbreviated herein as "DPPC."

In general, saturated acyl groups found in various lipids include groups having the trivial names propionyl, butanoyl, pentanoyl, caproyl, heptanoyl, capryloyl, nonanoyl, capryl, undecanoyl, lauroyl, tridecanoyl, myristoyl, pentadecanoyl, palmitoyl, phytanoyl, heptadecanoyl, stearoyl, nonadecanoyl, arachidoyl, heniecosanoyl, behenoyl, trucisanoyl and lignoceroyl. The corresponding IUPAC names for saturated acyl groups are trianoic, tetranoic, pentanoic, hexanoic, heptanoic, octanoic, nonanoic, decanoic, undecanoic, dodecanoic, tridecanoic, tetradecanoic, pentadecanoic, hexadecanoic, 3,7,11,15-tetramethylhexadecanoic, heptadecanoic, octadecanoic, nonadecanoic, eicosanoic, heneicosanoic, docosanoic, trocosanoic and tetracosanoic. Unsaturated acyl groups found in both symmetric and assymetric phosphatidylcholines include myristoleoyl, palmitoleoyl, oleoyl, elaidoyl, linoleoyl, linolenoyl, eicosenoyl and arachidonoyl. The corresponding IUPAC names for unsaturated acyl groups are 9-cis-tetradecanoic, 9-cis-hexadecanoic, 9-cis-octadecanoic, 9-trans-octadecanoic, 9-cis-12-cis-octadecadienoic, 9-cis-12-cis-15-cis-octadecatrienoic, 11-cis-eicosenoic and 5-cis-8-cis-11-cis-14-cis-eicosatetraenoic.

Alternately, U.S. Pat. No. 5,972,380 describes the use of "caged" phospholipids. Caged phospholipids are aminophospholipids that when present in a liposome, render the liposome pH-sensitive so that once endocytosed into target cells the caging groups are cleaved. This cleavage results in destabilization of the liposome, causing the uncaged lipids of the liposome to become fusogenic and to thereby release of the active agent carried by the liposome into the cell cytosome.

Exemplary phosphatidylethanolamines include dimyristoyl-phosphatidylethanolamine, dipalmitoyl-phosphatidylethanolamine, distearoyl-phosphatidylethanolamine, dioleoyl-phosphatidylethanolamine and egg phosphatidylethanolamine. Phosphatidylethanolamines may also be referred to under IUPAC naming systems as 1,2-diacyl-sn-glycero-3-phosphoethanolamines or 1-acyl-2-acyl-sn-glycero-3-phosphoeihanolamine, depending on whether they are symmetric or assymetric lipids.

Exemplary phosphatidic acids include dimyristoyl phosphatidic acid, dipalmitoyl phosphatidic acid and dioleoyl phosphatidic acid. Phosphatidic acids may also be referred to under IUPAC naming systems as 1,2-diacyl-sn-glycero-3-phosphate or 1-acyl-2-acyl-sn-glycero-3-phosphate, depending on whether they are symmetric or assymetric lipids.

Exemplary phosphatidylserines include dimyristoyl phosphatidylserine, dipalmitoyl phosphatidylserine, dioleoylphosphatidylserine, distearoyl phosphatidylserine, palmitoyl-oleylphosphatidylserine and brain phosphatidylserine. Phosphatidylserines may also be referred to under IUPAC naming systems as 1,2-diacyl-sn-glycero-3-[phospho-L-serine] or 1-acyl-2-acyl-sn-glycero-3-[phospho-L-serine], depending on whether they are symmetric or assymetric lipids. As used herein, the abbreviation "PS" refers to phosphatidylserine.

Exemplary phosphatidylglycerols include dilauryloylphosphatidylglycerol, dipalmitoylphosphatidylglycerol, distearoylphosphatidylglycerol, dioleoyl-phosphatidylglycerol, dimyristoylphosphatidylglycerol, palmitoyl-oleoyl-phosphatidylglycerol and egg phosphatidylglycerol. Phosphatidylglycerols may also be referred to under IUPAC naming systems as 1,2-diacyl-sn-glycero-3-[phospho-rac-(1-glycerol)] or 1-acyl-2-acyl-sn-glycero-3-[phospho-rac-(1-glycerol)], depending on whether they are symmetric or assymetric lipids. The phosphatidylglycerol 1,2-dimyristoyl-sn-glycero-3-[phospho-rac-(1-glycerol)] is abbreviated herein as "DMPG". The phosphatidylglycerol 1,2-dipalmitoyl-sn-glycero-3-(phospho-rac-1-glycerol) (sodium salt) is abbreviated herein as "DPPG".

Suitable sphingomyelins might include brain sphingomyelin, egg sphingomyelin, dipalmitoyl sphingomyelin, and distearoyl sphingomyelin Other suitable lipids include glycolipids, sphingolipids, ether lipids, glycolipids such as the cerebrosides and gangliosides, and sterols, such as cholesterol or ergosterol. As used herein, the term cholesterol is sometimes abbreviated as "Chol."

Additional lipids suitable for use in liposomes are known to persons of skill in the art and are cited in a variety of sources, such as 1998 McCutcheon's Detergents and Emulsifiers, 1998 McCutcheon's Functional Materials, both published by McCutcheon Publishing Co., New Jersey, and the Avanti Polar Lipids, Inc. Catalog.

Suitable lipids for use in the present invention will have sufficient long-term stability to achieve an adequate shelf-life. Factors affecting lipid stability are well-known to those of skill in the art and include factors such as the source (e.g. synthetic or tissue-derived), degree of saturation and method of storage of the lipid.

The overall surface charge of the liposome can affect the tissue uptake of a liposome. In certain embodiments of the present invention anionic phospholipids such as phosphatidylserine, phosphatidylinositol, phosphatidic acid, and cardiolipin will be suitable for use in the present invention. Also, neutral lipids such as dioleoylphosphatidyl ethanolamine (DOPE) may be used to target uptake of liposomes by specific tissues or to increase circulation times of intravenously administered liposomes. Further, cationic lipids may be used in the present invention for alteration of liposomal charge, where the cationic lipid can be included as a minor component of the lipid composition or as a major or sole component. Suitable cationic lipids typically have a lipophilic moiety, such as a sterol, an acyl or diacyl chain, and where the lipid has an overall net positive charge. Preferably, the head group of the lipid carries the positive charge.

One of skill in the art will select vesicle-forming lipid that achieve a specified degree of fluidity or rigidity. The fluidity or rigidity of the liposome can be used to control factors such as the stability of the liposome in serum or the rate of release of the entrapped agent in the liposome.

Liposomes having a more rigid lipid bilayer, or a liquid crystalline bilayer, are achieved by incorporation of a relatively rigid lipid. The rigidity of the lipid bilayer correlates with the phase transition temperature of the lipids present in the bilayer. Phase transition temperature is the temperature at which the lipid changes physical state and shifts from an ordered gel phase to a disordered liquid crystalline phase. Several factors affect the phase transition temperature of a lipid including hydrocarbon chain length and degree of unsaturation, charge and headgroup species of the lipid. Lipid having a relatively high phase transition temperature will produce a more rigid bilayer. Other lipid components, such as cholesterol, are also known to contribute to membrane rigidity in lipid bilayer structures. Cholesterol is widely used by those of skill in the art to manipulate the fluidity, elasticity and permeability of the lipid bilayer. It is thought to function by filling in gaps in the lipid bilayer. In contrast, lipid fluidity is achieved by incorporation of a relatively fluid lipid, typically one having a lower phase transition temperature. Phase transition temperatures of many lipids are tabulated in a variety of sources, such as Avanti Polar Lipids catalogue and Lipidat by Martin Caffrey, CRC Press.

Non-toxicity of the lipids is also a significant consideration in the present invention. Lipids approved for use in clinical applications are well-known to those of skill in the art. In certain embodiments of the present invention, synthetic lipids, for example, may be preferred over lipids derived from biological sources due to a decreased risk of viral or protein contamination from the source organism.

IV. Liposome Formation and Curcumin Entrapment

The formation and use of liposomes is generally known to those of skill in the art, as described in, e.g. Liposome Technology, Vols. 1, 2 and 3, Gregory Gregoriadis, ed., CRC Press, Inc; Liposomes: Rational Design, Andrew S. Janoff, ed., Marcel Dekker, Inc.; Medical Applications of Liposomes, D. D. Lasic and D. Papahadjopoulos, eds., Elsevier Press; Bioconjugate Techniques, by Greg T. Hermanson, Academic Press; and Pharmaceutical Manufacturing of Liposomes, by Francis J. Martin, in Specialized Drug Delivery Systems (Praveen Tyle, Ed.), Marcel Dekker, Inc.

The original method of forming liposomes (B angham et al., 1965, J. Mol. Biol. 13: 238-252) involved first suspending phospholipids in an organic solvent and then evaporating to dryness until a dry lipid cake or film is formed. An appropriate amount of aqueous medium is added and the lipids spontaneously form multilamellar concentric bilayer vesicles (also termed multilamellar vesicles (MLVs). These MLVs can then be dispersed by mechanical means. MLVs generally have diameters of from 25 nm to 4 µm. Sonication of MLVs results in the formation of small unilamellar vesicles (SUVs) with diameters in the range of 200 to 500 Å, containing an aqueous solution in the core. SUVs are smaller than MLVs and unilamellar.

While the original MLVs and SUVs were created using phospholipids, any of the lipid compositions described previously can be used to create MLVs and SUVs. When mixtures of lipids are used the lipids are typically co-dissolved in an organic solvent prior to the evaporation step of the process described above.

An alternate method of creating large unilamellar vesicles (LUVs) is the reverse-phase evaporation process, described, for example, in U.S. Pat. No. 4,235,871. This process generates reverse-phase evaporation vesicles (REVs), which are mostly unilamellar but also typically contain some oligolamellar vesicles. In this procedure a mixture of polar lipid in an organic solvent is mixed with a suitable aqueous medium. A homogeneous water-in-oil type of emulsion is formed and the organic solvent is evaporated until a gel is formed. The gel is then converted to a suspension by dispersing the gel-like mixture in an aqueous media.

Liposomes of the present invention may also be prepared wherein the liposomes have substantially homogeneous sizes in a selected size range. One effective sizing method for REVs and MLVs involves extruding an aqueous suspension of the liposomes through a series of polycarbonate membranes having a selected uniform pore size in the range of 0.03 to 0.2 micron, typically 0.05, 0.08, 0.1, or 0.2 microns. The pore size of the membrane corresponds roughly to the largest sizes of liposomes produced by extrusion through that membrane, particularly where the preparation is extruded two or more times through the same membrane. Homogenization methods are also useful for down-sizing liposomes to sizes of 100 nm or less (Martin, F. J., in Specialized Drug Delivery Systems-Manufacturing and Production Technology, (P. Tyle, Ed.) Marcel Dekker, New York, pp. 267-316 (1990)). Homogenization relies on shearing energy to fragment large liposomes into smaller ones. Other appropriate methods of down-sizing liposomes include reducing liposome size by vigorous agitation of the liposomes in the presence of an appropriate solubilizing detergent, such as deoxycholate.

Liposomes that have been sized to a range of about 0.2-0.4 microns may be sterilized by filtering the liposomes through a conventional sterilization filter, which is typically a 0.22 micron filter, on a high throughput basis. Other appropriate methods of sterilization will be apparent to those of skill in the art.

In certain embodiments, curcumin or curcumin analogues or metabolites can be incorporated into liposomes by several standard methods. Because curcumin is water-insoluble, it is possible to passively entrap curcumin or lipophilic curcumin analogues or metabolites by hydrating a lipid film or lipid emulsion that already contains an appropriate concentration of curcumin or a curcumin analogue. Alternately, curcumin or a curcumin analogue could be passively entrapped within the liposome by generating liposomes in a suitable polar solvent, such as ethanol, in which an appropriate concentration of curcumin or a curcumin analog has been dissolved, and subsequently dispersing the liposomes in an aqueous medium. Water-soluble curcumin analogues or metabolites could be passively entrapped by hydrating a lipid film with an aqueous solution of the agent.

In an alternate embodiment of the present invention, curcumin or curcumin analogues or metabolites can be conjugated to the surface of the liposomal bilayer. One well-known method of covalently attaching a drug to a liposome is the use of amide conjugation. For example, phospholipids having amine functional groups can be conjugated to one of the hydroxyl groups found in curcumin and various curcumin analogues or metabolites. Suitable lipids for amide conjugation to curcumin might include phosphatidylethanolamines and N-caproylamine-phosphatidylethanolamines. Curcumin analogues or metabolites containing other suitable functional groups, such as carboxyl groups or amine groups, can also be used in amide conjugation to a vesicle-forming lipid having a suitable functional group.

Phospholipids can form a variety of structures other than liposomes when dispersed in water, depending on the molar ratio of lipid to water. At low ratios the liposome is the preferred structure. The physical characteristics of liposomes depend on the pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

In addition to temperature, exposure to proteins can alter the permeability of liposomes. Certain soluble proteins such as cytochrome c bind, deform and penetrate the bilayer, thereby causing changes in permeability. Cholesterol inhibits this penetration of proteins, apparently by packing the phospholipids more tightly.

The ability to trap solutes varies between different types of liposomes. For example, MLVs are moderately efficient at trapping solutes, but SUVs are extremely inefficient. SUVs offer the advantage of homogeneity and reproducibility in size distribution, however, and a compromise between size and trapping efficiency is offered by large unilamellar vesicles (LUVs). These are prepared by ether evaporation and are three to four times more efficient at solute entrapment than MLVs.

In addition to liposome characteristics, an important determinant in entrapping compounds is the physicochemical properties of the compound itself. Polar compounds are trapped in the aqueous spaces and nonpolar compounds bind to the lipid bilayer of the vesicle. Polar compounds are released through permeation or when the bilayer is broken, but nonpolar compounds remain affiliated with the bilayer unless it is disrupted by temperature or exposure to lipoproteins. Both types show maximum efflux rates at the phase transition temperature.

V. Liposome Targeting Techniques

Liposomes interact with cells via four different mechanisms: (1) endocytosis by phagocytic cells of the reticuloendothelial system such as macrophages and neutrophils; (2) adsorption to the cell surface, either by nonspecific weak hydrophobic or electrostatic forces, or by specific interactions with cell-surface components; (3) fusion with the plasma cell membrane by insertion of the lipid bilayer of the liposome into the plasma membrane, with simultaneous release of liposomal contents into the cytoplasm; and (4) by transfer of liposomal lipids to cellular or subcellular membranes, or vice versa, without any association of the liposome contents. It often is difficult to determine which mechanism is operative and more than one may operate at the same time.

The fate and disposition of intravenously injected liposomes depend on their physical properties, such as size, fluidity and surface charge. They may persist in tissues for hours or days, depending on their composition, and half lives in the blood range from minutes to several hours. Larger liposomes, such as MLVs and LUVs, are taken up rapidly by phagocytic cells of the reticuloendothelial system, but physiology of the circulatory system restrains the exit of such large species at most sites. They can exit only in places where large openings or pores exist in the capillary endothelium, such as the sinusoids of the liver or spleen. Thus, these organs are the predominate site of uptake. On the other hand, SUVs show a broader tissue distribution but still are sequestered highly in the liver and spleen. In general, this in vivo behavior limits the potential targeting of liposomes to only those organs and tissues accessible to their large size. These include the blood, liver, spleen, bone marrow and lymphoid organs.

Smaller liposomes may exit the circulatory system at points where the endothelium has become "leaky". Solid tumors and inflammation sites often produce leaky endothelium that permits the extravasation of small liposomes. This effect is greatly enhanced by increasing the circulation times of the liposomes so that the liposomes may take advantage of this effect. One way of increasing the circulation time of liposomes is by using STEALTH® liposomes. STEALTH® liposomes are typically derivatized with a hydrophilic polymer chain or polyalkylether, such as polyethyleneglycol (PEG). (See, for example, U.S. Pat. Nos. 5,013,556, 5,213,804, 5,225,212 and 5,395,619, herein incorporated by reference.) The polymer coating reduces the rate of uptake of liposomes by macrophages and thereby prolongs the presence of the liposomes in the blood stream. This can also be used as a mechanism of prolonged release for the drugs carried by the liposomes, (see e.g. Woodle et al., 1992). In the present invention, therefore, it will be desirable in certain embodiments that liposomal curcumin be delivered by a STEALTH®-liposome-type derivatized liposome formulation such as PEGylated liposomes. PEGylated liposomes are also referred to herein as sterically-stabilized liposomes or "SSL," in contrast to non-PEGylated liposomes which are referred to as conventional liposomes or "CL."

Polyethylene glycol-lipid conjugates can be produced using a variety of lipids. Pegylated lipids that are currently commercially available include the phosphatidylethanolamines 1,2-diacyl-sn-glycero-3-phosphoethanolamine-N-[methoxy(polyethylene glycol)-550], 1,2-diacyl-sn-glycero-3-phosphoethanolamine-N-[methoxy(polyethylene glycol)-750], 1,2-diacyl-sn-glycero-3-phosphoethanolamine-N-[methoxy(polyethylene glycol)-1000], 1,2-diacyl-sn-glycero-3-phosphoethanolamine-N-[methoxy(polyethylene glycol)-2000], 1,2-diacyl-sn-glycero-3-phosphoethanolamine-N-[methoxy(polyethylene glycol)-3000] and 1,2-diacyl-sn-glycero-3-phosphoethanolamine-N-[methoxy(polyethylene glycol)-5000]. As used herein, "DMPE-PEG-2000" stands for 1,2-dimyristoyl-sn-glycero-3-phosphoethanolamine-N-[methoxy (polyethylene glycol)-2000] (ammonium salt). As used herein, "DSPE-PEG-2000" stands for 1,2-distearoyl-sn-glycero-3-phosphoethanolamine-N-[methoxy (polyethylene glycol)-2000] (ammonium salt).

In other embodiments, it may further be desirable to target curcumin delivery to specific tissues, particularly tumor tissues. Should specific targeting be desired, methods are available for this to be accomplished. Targeting ligands such as antibodies or antibody fragments can be used to bind to the liposome surface and to direct the antibody and its drug contents to specific antigenic receptors located on a particular cell-type surface. (See e.g., Mastrobattista et al., 1999) Carbohydrate determinants (glycoprotein or glycolipid cell-surface components that play a role in cell-cell recognition, interaction and adhesion) can also be used as targeting ligands as they have potential in directing liposomes to particular cell types. Certain proteins can be used as targeting ligands, usually ones that are recognized by self-surface receptors of the targeted tissue. For example, a ligand that binds to a cell-surface receptor that is overexpressed in particular cancer cells might be used to increase uptake of liposomes by the target tissue. Cell surface receptors that are endocytosed will be preferred in certain embodiments. When combined with "stealth" technology, the targeting ligand is often attached to the end of the hydrophilic polymer that is exposed to the aqueous medium. Alternately, liposomes can incorporate fusogenic proteins, e.g. fusogenic proteins derived from viruses, which induce fusion of the liposome with the cellular membrane.

As used herein, targeting ligands are any ligand which causes liposomes to associate with the target cell-type to an enhanced degree over non-targeted tissues. In certain embodiments, the targeting ligand is a cell surface receptor that is endocytosed by the target cell. Appropriate targeting ligands for use in the present invention include any ligand that causes increased binding or association of liposomes with cell-surface of the target cells over non-target cells, including antibodies, antibody fragments, carbohydrate determinants, or proteins, preferably proteins that are recognized by cell-surface receptors or fusogenic proteins.

Passive targeting of liposomes relies on non-specific release of the drug payload over time, and does not rely on the use of targeting ligands. Targeting-ligand containing liposomes however can achieve cytosolic delivery of curcumin or curcumin analogues or metabolites by a number of additional mechanisms. Liposomes can be actively targeted to a particular cell type, and release the contents of the liposome extracellularly in the vicinity of the target tissue, or transfer lipophilic compounds directly from the liposome to the cell membrane. Alternately, the target-ligand containing liposome can bind to a cell surface receptor that is endocytosed, which would permit intracellular release of the liposomal drug payload. Fusogenic peptides or pH-sensitive liposomes are particularly useful in this context to trigger release of the liposomal contents from the endosome into the cytoplasm.

VI. Polymeric Drug Delivery Systems

The present invention also provides that curcumin or curcumin analogue can be encapsulated within a protective wall material that is polymeric in nature rather than lipid-based. The polymer used to encapsulate the bioactive agent is typically a single copolymer or homopolymer. The polymeric drug delivery system may be colloidal or non-colloidal in nature.

Colloidal polymeric encapsulation structures include microparticles, microcapsules, microspheres, nanoparticles, nanocapsules and nanospheres, block copolymer micelles, or any other encapsulated structure. Both synthetic polymers, which are made by man, and biopolymers, including proteins and polysaccharides, can be used in the present invention. The polymeric drug delivery system may be composed of biodegradable or non-biodegradable polymeric materials, or any combination thereof.

"Microparticles" (or "microspheres") means a solid object, essentially of regular or semi-regular shape, that is more than about one micrometer in its largest diameter and exhibits a liquid core and semipermeable polymeric shell. Microparticles or microspheres typically have a diameter of from about 1 to 2,000 µm (2 mm), normally ranging from about 100 to 500 µm.

"Nanoparticle" (or "nanosphere") means a submicroscopic solid object, essentially of regular or semi-regular shape, that is less than one micrometer in its largest dimension and exhibits a liquid core and a semipermeable polymeric shell. Nanoparticles or nanospheres typically range from about 1 to 1,000 nanometers (nm). Normally, nanoparticles range from about 100 to 300 nm.

Microcapsule" means a microscopic (few micrometers in size to few millimeters) solid object of from a few micrometers to a few millimeters in size that is of essentially regular cylindrical shape and exhibits a liquid core and a semipermeable polymeric shell.

"Nanocapsules" means a solid object of less than about one micrometer in size that is essentially regular in shape and which exhibits a liquid core and a semipermeable polymeric shell.

Block copolymer micelles are formed from two or more monomeric units which, following polymerization, are arranged in a specific manner depending on the type of copolymer desired. Micelles are formed from individual block copolymer molecules, each of which contains a hydrophobic block and a hydrophilic block. The amphiphilic nature of the block copolymers enables them to self-assemble to form nanosized aggregates of various morphologies in aqueous solution such that the hydrophobic blocks form the core of the micelle, which is surrounded by the hydrophilic blocks, which form the outer shell (Zhang L. Eisenberg A. (1995) Science, 268:1728-1731; Zhang L, Yu K., Eisenberg A. (1996) Science, 272:1777-1779). The inner core of the micelle creates a hydrophobic microenvironment for the non-polar drug, while the hydrophilic shell provides a stabilizing interface between the micelle core and the aqueous medium. The properties of the hydrophilic shell can be adjusted to both maximnize biocompatibility and avoid reticuloendothelial system uptake and renal filtration. The size of the micelles is usually between 10 nm and 100 nm.

Non-colloidal polymeric drug-delivery systems including films, hydrogels and "depot" type drug delivery systems are also contemplated by the present invention. Such non-colloidal polymeric systems can also be used in the present invention in conjunction with parenteral injection, particularly where the non-colloidal drug delivery system is placed in proximity to the targeted cancerous tissue.

"Hydrogel" means a solution of polymers, sometimes referred to as a sol, converted into gel state by small ions or polymers of the opposite charge or by chemical crosslinking.

"Polymeric film" means a polymer-based film generally from about 0.5 to 5 mm in thickness which is sometimes used as a coating.

In certain embodiments the microparticles, nanoparticles, microcapsules, block copolymer micelles or other polymeric drug delivery systems comprising curcumin or a curcumin analogue can be coupled with a targeting or binding partner. By linking the polymeric drug delivery system to one or more binding proteins or peptides, delivery of the encapsulated therapeutic agent can be directed to a target cell population which binds to the binding protein or peptide.

VII. Pharmaceutical Compositions

As used herein, the term 'pharmaceutically acceptable' (or 'pharmacologically acceptable') refers to molecular entities and compositions that do not produce an adverse, allergic or other untoward reaction when administered to an animal or a human, as appropriate. The term 'pharmaceutically acceptable carrier', as used herein, includes any and all solvents, dispersion media, coatings, antibacterial, isotonic and absorption delaying agents, buffers, excipients, binders, lubricants, gels, surfactants and the like, that may be used as a media for a pharmaceutically acceptable substance.

Pharmaceutical compositions of the present invention comprising curcumin or a curcumin analogue and a colloidal drug delivery carrier such as a liposome are prepared according to standard techniques. (As used herein, the abbreviation "L-cur" refers to liposomal curcumin compositions.) They can further comprise a pharmaceutically acceptable carrier. Generally, a pharmaceutical carrier such as normal saline will be employed. Other suitable carriers include water, buffered water, isotonic aqueous solutions, 0.4% saline, 0.3% aqueous glycine and the like, including glycoproteins for enhanced stability, such as albumin, lipoprotein and globulin. These compositions can be sterilized by conventional sterilization techniques that are well-known to those of skill in the art. Sufficiently small liposomes, for example, can be sterilized using sterile filtration techniques.

Formulation characteristics that can be modified include, for example, the pH and the osmolality. For example, it may be desired to achieve a formulation that has a pH and osmolality similar to that of human blood or tissues to facilitate the formulation's effectiveness when administered parenterally. Alternatively, to promote the effectiveness of the disclosed compositions when administered via other administration routes, alternative characteristics may be modified.

Buffers are useful in the present invention for, among other purposes, manipulation of the total pH of the pharmaceutical formulation (especially desired for parenteral administration). A variety of buffers known in the art can be used in the present formulations, such as various salts of organic or inorganic acids, bases, or amino acids, and including various forms of citrate, phosphate, tartrate, succinate, adipate, maleate, lactate, acetate, bicarbonate, or carbonate ions. Particularly advantageous buffers for use in parenterally administered forms of the presently disclosed compositions in the present invention include sodium or potassium buffers, particularly sodium phosphate. In a preferred embodiment for parenteral dosing, sodium phosphate is employed in a concentration approximating 20 mM to achieve a pH of approximately 7.0. A particularly effective sodium phosphate buffering system comprises sodium phosphate monobasic monohydrate and sodium phosphate dibasic heptahydrate. When this combination of monobasic and dibasic sodium phosphate is used, advantageous concentrations of each are about 0.5 to about 1.5 mg/ml monobasic and about 2.0 to about 4.0 mg/ml dibasic, with preferred concentrations of about 0.9 mg/ml monobasic and about 3.4 mg/ml dibasic phosphate. The pH of the formulation changes according to the amount of buffer used.

Depending upon the dosage form and intended route of administration it may alternatively be advantageous to use buffers in different concentrations or to use other additives to adjust the pH of the composition to encompass other ranges. Useful pH ranges for compositions of the present invention include a pH of about 2.0 to a pH of about 12.0.

In some embodiments, it will also be advantageous to employ surfactants in the presently disclosed formulations, where those surfactants will not be disruptive of the drug-delivery system used. Surfactants or anti-adsorbants that prove useful include polyoxyethylenesorbitans, polyoxyethylenesorbitan monolaurate, polysorbate-20, such as Tween-20TM, polysorbate-80, hydroxycellulose, and genapol. By way of example, when any surfactant is employed in the present invention to produce a parenterally administrable composition, it is advantageous to use it in a concentration of about 0.01 to about 0.5 mg/ml.

Additional useful additives are readily determined by those of skill in the art, according to particular needs or intended uses of the compositions and formulator. One such particularly useful additional substance is sodium chloride, which is useful for adjusting the osmolality of the formulations to achieve the desired resulting osmolality. Particularly preferred osmolalities for parenteral administration of the disclosed compositions are in the range of about 270 to about 330 mOsm/kg. The optimal osmolality for parenterally administered compositions, particularly injectables, is approximately 300 Osm/kg and achievable by the use of sodium chloride in concentrations of about 6.5 to about 7.5 mg/ml with a sodium chloride concentration of about 7.0 mg/ml being particularly effective.

Curcumin-containing liposomes or curcumin-containing colloidal drug-delivery vehicles can be stored as a lyophilized powder under aseptic conditions and combined with a sterile aqueous solution prior to administration. The aqueous solution used to resuspend the liposomes can contain pharmaceutically acceptable auxiliary substances as required to approximate physical conditions, such as pH adjusting and buffering agents, tonicity adjusting agents and the like, as discussed above.

In other embodiments the curcumin-containing liposomes or curcumin-containing colloidal drug-delivery vehicle can be stored as a suspension, preferable an aqueous suspension, prior to administration. In certain embodiments, the solution used for storage of liposomes or colloidal drug carrier suspensions will include lipid-protective agents which protect lipids against free-radical and lipid-peroxidative damage on storage. Suitable protective compounds include free-radical quenchers such as alpha-tocopherol and water-soluble iron-specific chelators, such as ferrioxamine.

VIII. Administration of Curcumin or Curcumin Analogues or Metabolites

Mostly, it is contemplated liposomes or other colloidal drug-delivery vehicles containing curcumin or a curcumin analogue would be administered by intravenous injection, but other routes of parenteral administration are also conceivable, particularly those that enhance contact of the liposomes or colloidal drug-delivery vehicles with the target tissue. Methods of parenteral administration that can be employed in the present invention also include intraarterial, intramuscular, subcutaneous, intra-tissue, intranasal, intradermal, instillation, intracerebral, intrarectal, intravaginal, intraperitoneal, intratumoral, juxtaposition of tumor and administration directly to the lesion.

In addition, the formulations can also be used as a depot preparation. Such long acting formulations may be administered by implantation at an appropriate site or by parenteral injection, particularly intratumoral injection or injection at a site adjacent to cancerous tissue.

In alternate embodiments, the formulations of the present invention may be administered to a mammalian subject, including a human patient, using buccal, sublingual, suppository, topical, inhalant or aerosolized routes of administration.

The colloidal drug-delivery system, such as a liposome, containing curcumin or a curcumin analogue can then be administered to a mammal having a tumor or other cancerous growth. Animal studies to date have never reached an LD50 for free curcumin administration. Oral doses of free curcumin as high as 500 mg/kg and intravenous doses of 40 mg/kg have been administered in rats. (Ireson, 2001). Absorption is minimal after oral dosing and free curcumin disappears from the circulation usually less than one hour after intravenous dosing. Intravenous. administration of liposomal curcumin has been tolerated by mice at doses of approximately 40 mg/kg of body weight and no LD50 value has been reached. In the present invention, when curcumin is encapsulated in liposomes or other colloidal drug-delivery vehicle, any effective amount of the liposomal curcumin may be administered, preferably doses of approximately 10-200 mg of curcumin per kg body weight, and most preferably 40-100 mg/kg.

The following examples are included to demonstrate preferred embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

The surprising utility of liposomal curcumin or curcumin analogues or metabolites in treating certain cancers is attributable to the potent antiproliferative and proapoptotic effects of curcumin compositions on those cancer cells. The use of colloidal drug-delivery systems such as liposomes allows the administration of an effective dose of curcumin or curcumin analogue in vivo for the treatment of cancer. The following working examples are illustrative only, and are not intended to limit the scope of the invention.

Example 1

Preparation of curcumin-containing liposomes. Liposomal curcumin was formulated using the following protocol. A phospholipid, 1,2-dimyristoyl-sn-glycero-3-phosphocholine (dimyristoylphosphocholine; DMPC) (Avanti Polar Lipids, Alabaster, Ala. 35007) was chosen for the liposomal formulation. The phospholipid was solubilized by dissolving 200 mg of DMPC in 10 ml of t-butanol (Fisher Scientific) and heating the mixture in a 37° C. water bath for 5 minutes. The solution was stored at −20° C. in a container that protected the solution from exposure to light.

Curcumin (Sigma) was solubilized by dissolving curcumin in DMSO to a final concentration of 50 mg/ml. The solution was also aliquoted and stored in a container that protected the solution from exposure to light.

To combine the phospholipid and curcumin solutions, 10 ml of DMPC in t-butanol, 0.4 ml curcumin in DMSO and 90 ml of t-butanol were mixed very well and aliquoted into small sterile glass vials containing 2.5 mls of solution each. The vials of solution were frozen in a dry ice-acetone bath and lyophilized overnight using a FTS Systems corrosion-resistant Freeze-Dryer (Stone Ridge, N.Y.). The dried lipid mixtures were stored at −20° C.

Prior to use, the desired amount of 0.9% NaCl was used to resuspend the lipid mixtures.

Example 2

Curcumin inhibits proliferation/survival of pancreatic cells. Seventy-two hours of exposure to free curcumin inhibited pancreatic cell growth of all five lines tested in a concentration-dependent manner. Controls were exposed to 0.1% v/v DMSO. Proliferation and survival of the pancreatic cells were assessed by MTT assay, a standard colorimetric assay used to measure cell survival and proliferation (Mosman, 1983). MTT (3-[4,5-cimethylthiazol-2-yl]-2,5-diphenyl tetrazolium bromide) is cleaved by living cells to yield a dark blue formazan product. The color is quantitated by spectrophotometer and reflects cellular proliferation and survival. As shown in FIGS. 1-5, pancreatic Bxpc-3, Capan-1, Capan-2, HS766-T and ASPC-1 cells were exposed to free curcumin in varying concentrations for a period of 72 hours. The control for each assay was exposed to 0.1% v/v DMSO.

Example 3

Liposomal curcumin has equivalent or greater anti-proliferative effects than free curcumin. The inventors have examined the effect of free curcumin on the proliferation and survival of five pancreatic carcinoma cell lines (Bxpc-3, Capan-1, Capan-2, HS766T, and Aspc-1). The effects of liposomal curcumin were compared to those of liposomes alone, free curcumin, lyophilized free curcumin and liposomal curcumin. MTT proliferation/survival assay was performed after 72 hours of incubation.

Exposure to curcumin resulted in significant inhibition of proliferation and survival as assessed by MTT assay in all of these cell lines. FIGS. 5-10 show graphs of the results of the assays using Bxpc-3, Capan-1, Capan-2, HS766-1 and ASPC-1 cell lines, respectively. In the MTT proliferation/survival assay shown in FIGS. 5-10 the pancreatic cell lines were exposed to free curcumin, lyophilized free curcumin (lyophilized curcumin), liposomal curcumin or liposomes without curcumin (liposomes). The MTT assay was performed after pancreatic cells were exposed for 72 hours to each compound at concentrations ranging from 0 to 5 μg/ml.

Table I indicates the $IC_{50}$ and $IC_{90}$ values calculated from the assays of the effects of both free and liposomal curcumin.

TABLE I

Inhibitory Concentration of Free vs. Liposomal Curcumin MTT Assay (72 hours incubation)

| Name of Cells | $IC_{50}$ of free curcumin | $IC_{50}$ of liposomal curcumin | $IC_{90}$ of free curcumin | $IC_{90}$ of liposomal curcumin |
|---|---|---|---|---|
| BXPC-3 | 2 μg/ml | 2 μg/ml | 5 μg/ml | 5 μg/ml |
|  | 5.4 μM | 5.4 μM | 13.5 μM | 13.5 μM |
| CAPAN-1 | 2 μg/ml | 0.75 μg/ml | 5 μg/ml | 2.5 μg/ml |
|  | 5.4 μM | 2 μM | 13.5 μM | 6.75 μM |
| CAPAN-2 | 17 μg/ml | 14 μg/ml | 35 μg/ml | 35 μg/ml |
|  | 46 μM | 37.8 μM | 94.5 μM | 94.5 μM |
| HS766-T | 2.6 μg/ml | 2.5 μg/ml | 8 μg/ml | 9 μg/ml |
|  | 7 μM | 6.75 μM | 21.6 μM | 24 μM |
| ASPC-1 | 4 μg/ml | 4 μg/ml | 10 μg/ml | 10 μg/ml |
|  | 10.8 μM | 10.8 μM | 27 μM | 27 μM |

The 50% inhibitory concentration ($IC_{50}$) of free curcumin varied from approximately 5 μm in Capan-1 and BxPC-3 cells to about 46 μM in Capan-2 cells. The 50% inhibitory concentration ($IC_{50}$) of liposomal curcumin varied from approximately 2 μm in Capan-1 cells to about 38 μM in Capan-2 cells. The 90% inhibitory concentration ($IC_{90}$) of free curcumin varied from approximately 14 μm in Capan-1 and BxPC-3 cells to about 95 μM in Capan-2 cells. The 90% inhibitory concentration ($IC_{90}$) of liposomal curcumin varied from approximately 7 μm in Capan-1 cells to about 95 μM in Capan-2 cells. The results demonstrate that the growth inhibitory effects of liposomal curcumin were approximately equal to or better than that of free curcumin. Empty liposomes had minimal growth/survival suppressive effects.

Example 4

The Growth Inhibitory Effects of Liposomal Curcumin are Irreversible. Pancreatic cell recovery of proliferation and survival after exposure to liposomal curcumin was determined for Bxpc-3, Capan-1, Capan-2, HS766-1 and ASPC-1 cell lines, respectively. Pancreatic cells were grown on standard media. One control was untreated pancreatic cells. Another control was pancreatic cells treated with 0.1% DMSO, the solvent used to dissolve free curcumin. In addition to the controls, pancreatic cells were treated with empty liposomes or liposomal curcumin for 72 hours. The concentrations of liposomal curcumin used were approximately the $IC_{50}$ and $IC_{90}$ for each cell line (as determined in Example 3). After exposure, cells were replated in fresh media and allowed to recover in the absence of curcumin or liposomes. Recovery of proliferation/survival was assessed after an additional 72 hours. The cells were assayed by MTT assay 72 hours after replating and the results are shown in FIGS. 11-15.

Figure 11:
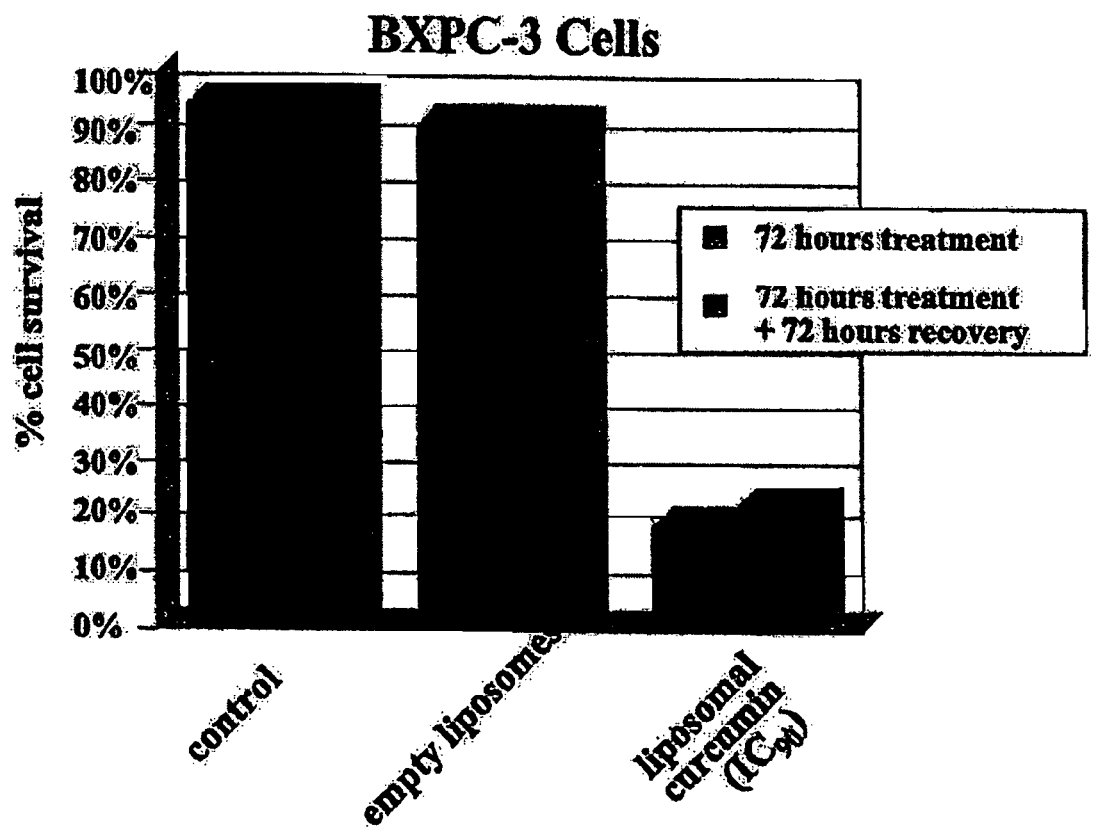
FIG. 11 Pancreatic BxPC-3 cell recovery of proliferation and survival after exposure to liposomal curcumin.

The sets of bars of the graph in FIG. 11 (left to right) correspond to control BxPC-3 cells followed by BxPC-3 cells exposed to empty liposomes or to 5 μg/ml (13.5 μM) liposomal curcumin, the latter being the $IC_{90}$ concentration of liposomal curcumin for BxPC-3 cells. The left bar of each pair corresponds to assay results after 72 hours of treatment. The right bar corresponds to assay results after 72 hours of treatment plus 72 hours recovery on fresh media without treatment.

Figure 12:
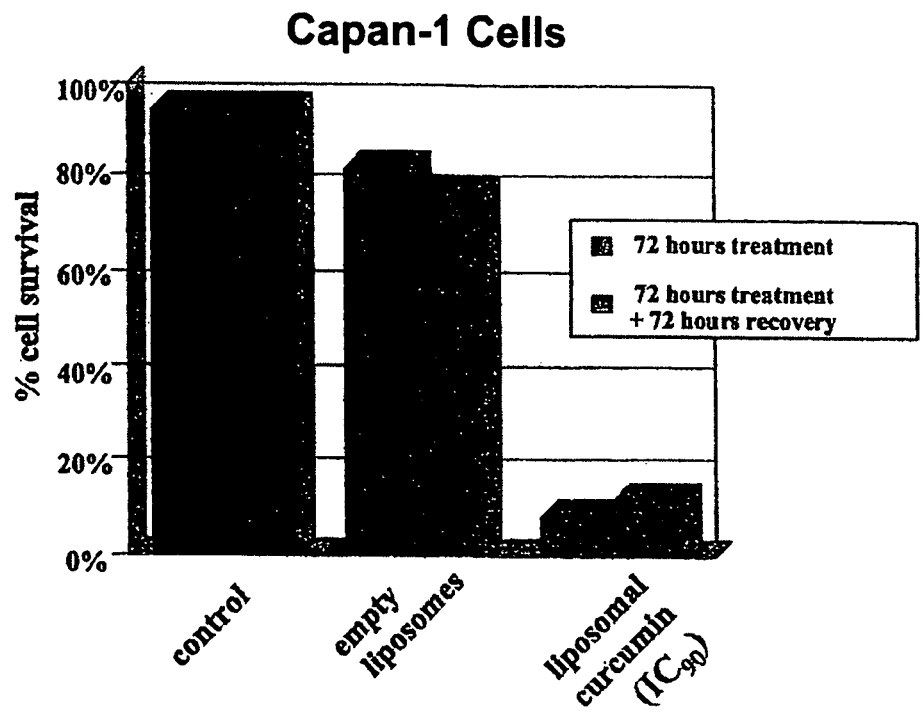
FIG. 12 Pancreatic Capan-1 cell recovery of proliferation and survival after exposure to liposomal curcumin.

The sets of bars of the graph in FIG. 12 (left to right) correspond to control Capan-1 cells followed by Capan-1 cells exposed to empty liposomes or to 2.5 μg/ml (6.75 μM liposomal curcumin), the latter being the $IC_{90}$ concentration of liposomal curcumin for Capan-1 cells. The left bar of each pair corresponds to assay results after 72 hours of treatment. The right bar corresponds to assay results after 72 hours of treatment plus 72 hours recovery on fresh media without treatment.

Figure 13:
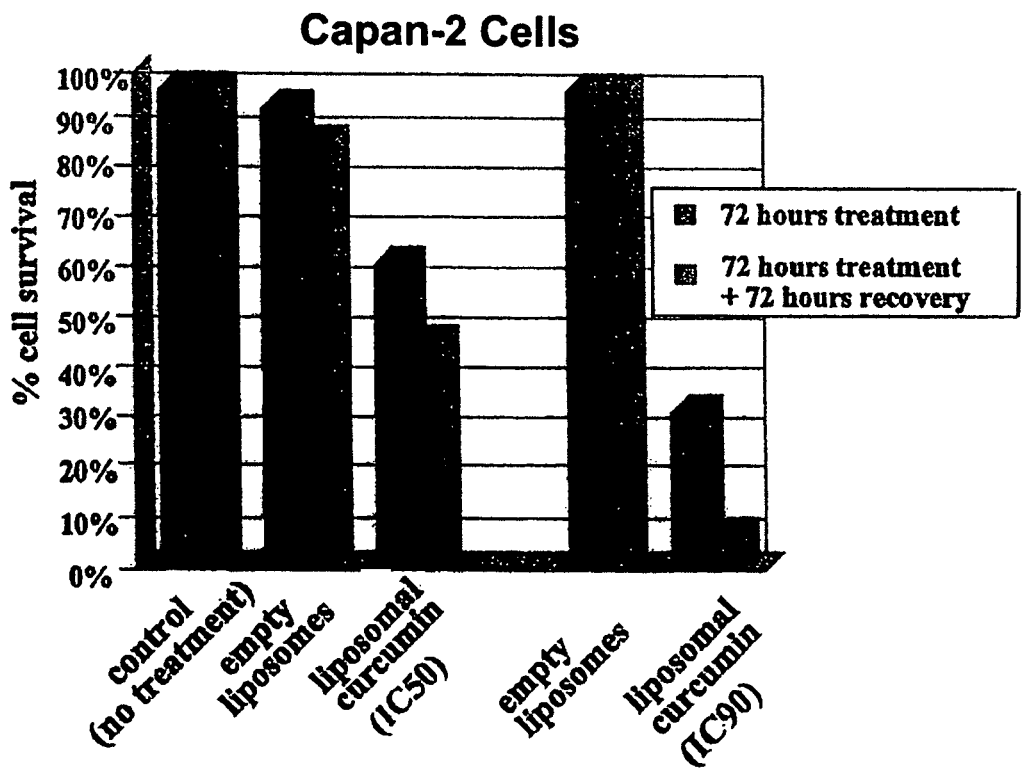
FIG. 13 Pancreatic Capan-2 cell recovery of proliferation and survival after exposure to liposomal curcumin.

In FIG. 13, the sets of bars of the graph (left to right) correspond to control Capan-2 cells followed by Capan-2 cells exposed to empty liposomes, 14 µg/ml (37.8 µM) liposomal curcumin, empty liposomes, and 35 µg/ml (94.5 µM) liposomal curcumin. 37.8 µM represents the $IC_{50}$ and 94.5 µM represents the $IC_{90}$ for liposomal curcumin for Capan-2 cells. (The amount of empty liposomes is equivalent to the amount of liposomal material in the corresponding experiments with liposomal curcumin, i.e. the $IC_{50}$ and $IC_{90}$ levels, respectively.) The left bar of each pair corresponds to assay results after 72 hours of treatment. The right bar corresponds to assay results after 72 hours of treatment plus 72 hours recovery on fresh media without treatment.

Figure 14:
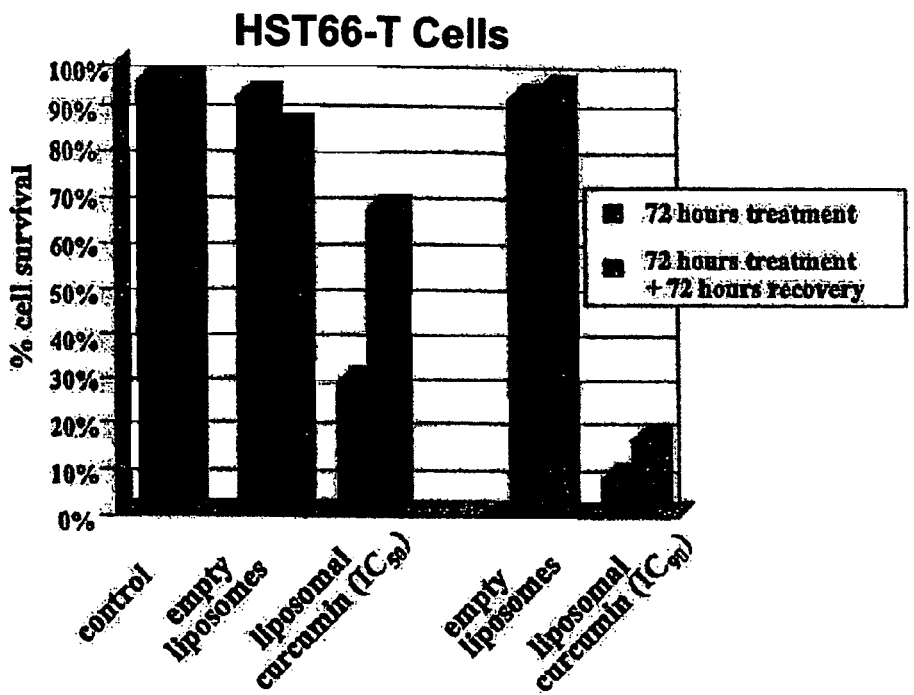
FIG. 14 Pancreatic HS766-T cell recovery of proliferation and survival after exposure to liposomal curcumin.

In FIG. 14, the sets of bars of the graph (left to right) correspond to control HS766-T cells followed by HS766-T cells exposed to empty liposomes, 2.5 µg/ml (6.75 µM) liposomal curcumin, empty liposomes, and 9 µg/ml (24 µM) liposomal curcumin. 6.75 µM represents the $IC_{50}$ and 24 µM represents the $IC_{90}$ for liposomal curcumin for HS766-T cells. (The amount of empty liposomes is equivalent to the amount of liposomal material in the corresponding experiments with liposomal curcumin, i.e. the $IC_{50}$ and $IC_{90}$ levels, respectively.) The left bar of each pair corresponds to assay results after 72 hours of treatment. The right bar corresponds to assay results after 72 hours of treatment plus 72 hours recovery on fresh media without treatment.

Figure 15:
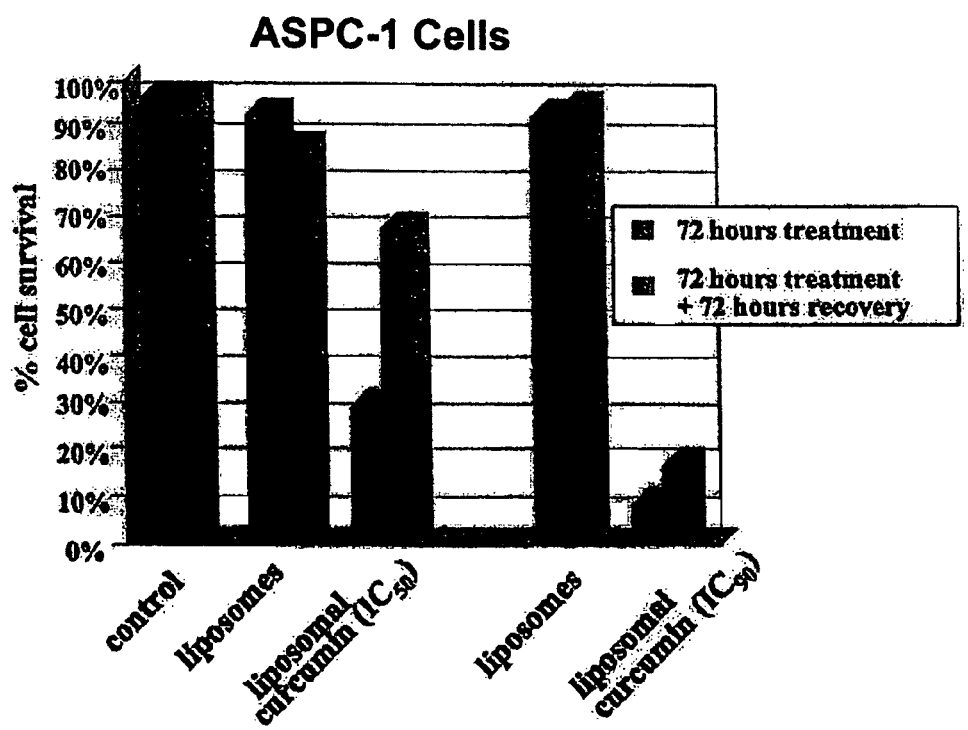
FIG. 15 Pancreatic ASPC-1 cell recovery of proliferation and survival after exposure to liposomal curcumin.

In FIG. 15, the sets of bars of the graph (left to right) correspond to control ASPC-1 cells followed by ASPC-1 cells exposed to empty liposomes, 4 µg/ml (10.8 µM) liposomal curcumin, empty liposomes, and 10 µg/ml (27 µM) liposomal curcumin. 4 µM represents the $IC_{50}$ and 27 µM represents the $IC_{90}$ for liposomal curcumin for ASPC-1 cells. (The amount of empty liposomes is equivalent to the amount of liposomal material in the corresponding experiments with liposomal curcumin, i.e. the $IC_{50}$ and $IC_{90}$ levels, respectively.) The left bar of each pair corresponds to assay results after 72 hours of treatment. The right bar corresponds to assay results after 72 hours of treatment plus 72 hours recovery on fresh media without treatment.

As shown by FIGS. 11-15, there was a concentration-dependent loss of ability to recover, indicating that the effect of liposomal curcumin was not merely cytostatic, but rather resulted in induction of apoptosis or cell death.

Example 5

Both Free and Liposomal Curcumin Induce Apoptosis in Pancreatic Cancer. Apoptosis of pancreatic cells was assessed by Annexin-V/Proopidium iodide staining (FACS analysis) after 72 hours of exposure to a DMSO control, empty liposomes, free curcumin or liposomal curcumin. Apoptosis assay was performed using either pancreatic BxPC-3 or HS766-T cells. The cells were exposed to either a control of 0.1% DMSO, empty liposomes, free curcumin or liposomal curcumin for 72 hours. Free curcumin and liposomal curcumin were administered in concentrations equal to either the $IC_{50}$ or $IC_{90}$ of liposomal curcumin. After incubation for 72 hours, the cells were assayed using Annexin-V/Proopidium iodide staining (FACS analysis) to determine how much apoptosis had occurred.

Figure 16:
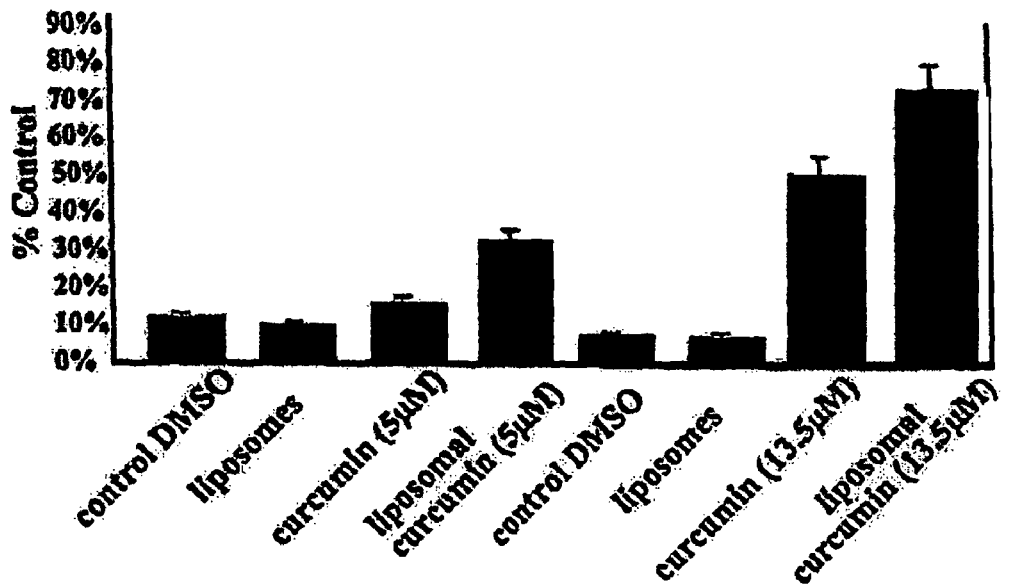
FIG. 16 Apoptosis assay of the effects of liposomal curcumin on pancreatic BxPC-3 cells.

For FIG. 16, bars for free and liposomal curcumin on the left side of the graph correspond to a concentration of curcumin if 5 µM, which is the $IC_{50}$ for liposomal curcumin in BxPC-3 cells. Bars for fee and liposomal curcumin on the right side of the graph correspond to a concentration of curcumin of 13.5 µM, which is the $IC_{90}$ for liposomal curcumin in BxPC-3 cells.

Figure 17:
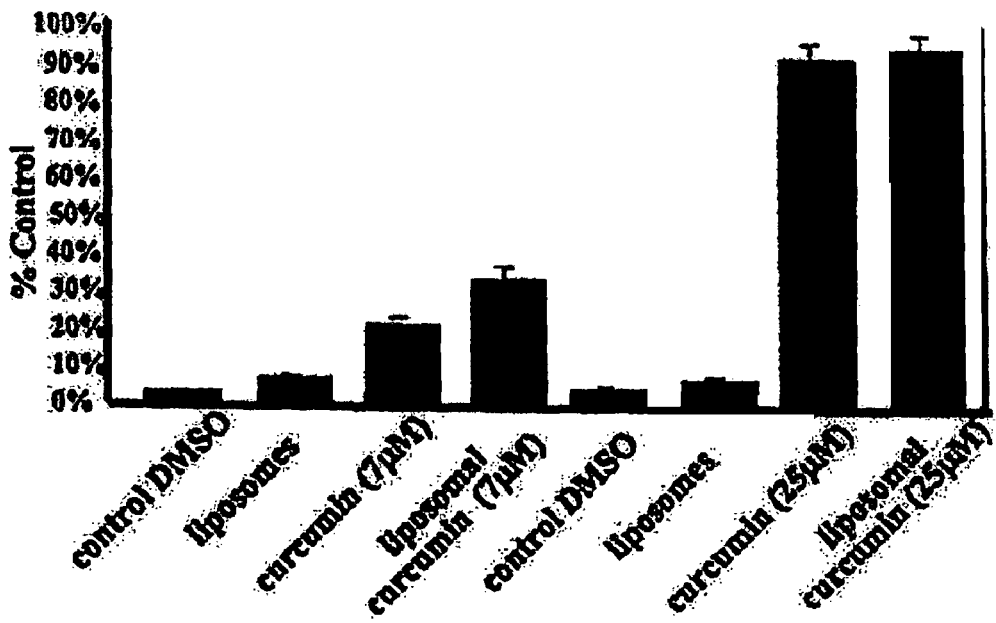
FIG. 17 Apoptosis assay of the effects of liposomal curcumin on pancreatic HS766-T cells.

For FIG. 17, bars for free and liposomal curcumin on the left side of the graph correspond to a concentration of curcumin if 7 µM, which is the $IC_{50}$ for liposomal curcumin in HS766-T cells. Bars for fee and liposomal curcumin on the right side of the graph correspond to a concentration of curcumin of 25 µM, which is the $IC_{90}$ for liposomal curcumin in HS766-T cells.

As can be seen in FIGS. 16 and 17, there was dose-related apoptosis after treatment with either free curcumin or liposomal curcumin. Apoptotic induction by liposomal curcumin greater than that of free curcumin at both the $IC_{50}$ and $IC_{90}$ for liposomal curcumin. Empty liposomes had no significant apoptotic effect. At the $IC_{90}$ for liposomal curcumin (as determined in Example 3) liposomal curcumin induced 73% to 93% apoptosis after 72 hours.

Example 6

Figure 18:
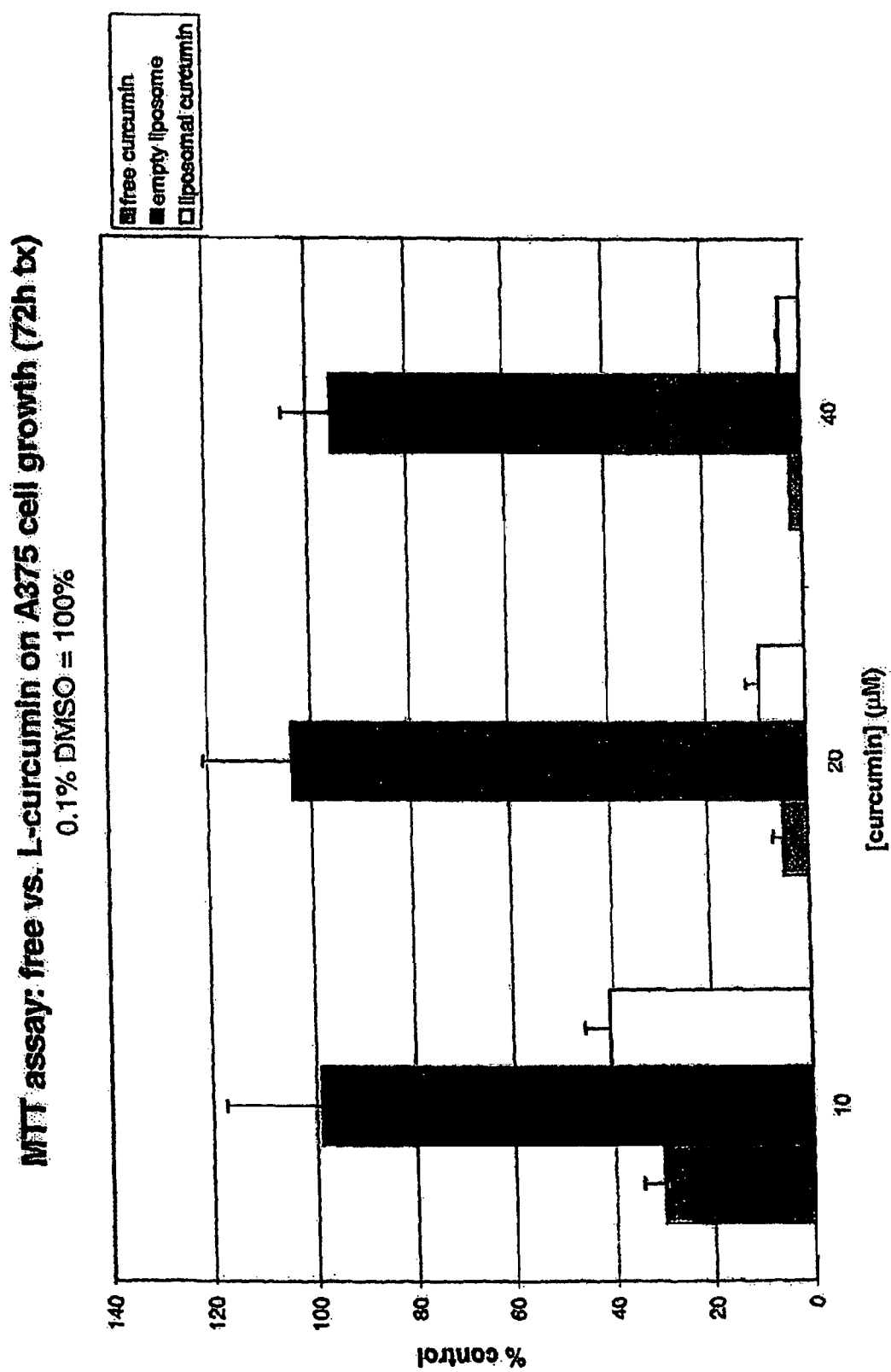
FIG. 18 MTT assay of the effects of liposomal curcumin on melanoma A375 cells.
Figure 19:
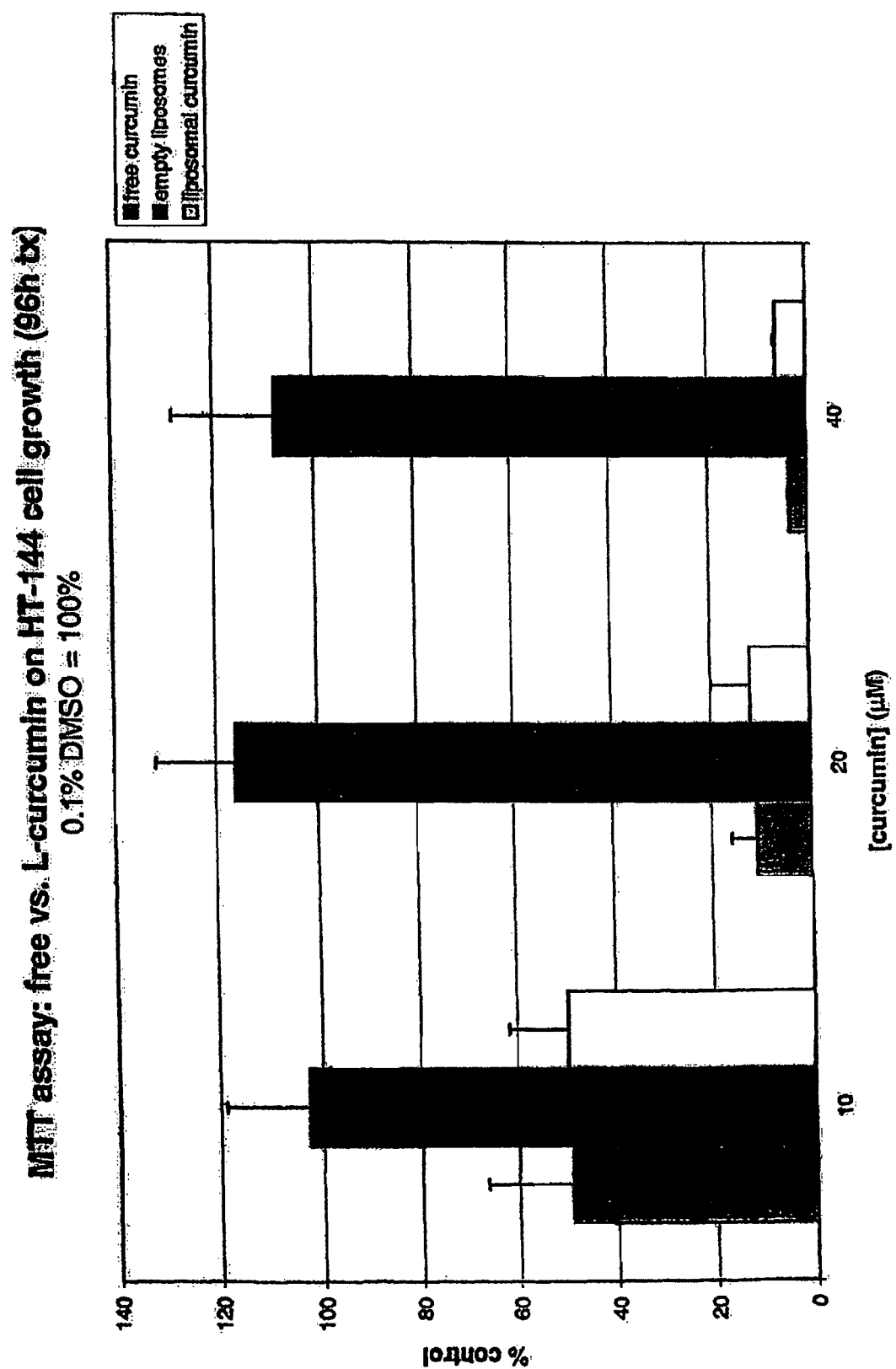
FIG. 19 MTT assay of the effects of liposomal curcumin on melanoma HT-144 cells.

Liposomal curcumin has anti-proliferative effects on melanoma cells. Liposomal curcumin was shown to have antiproliferative and apoptotic effects on two melanoma cell lines, HT-144 and A375, approximately equivalent to that of free curcumin. Cells were grown in the presence 0.1% DMSO (control), free curcumin, empty liposomes or liposomal curcumin for 72 or 96 hours. Free curcumin and liposomal curcumin were administered at concentrations of 10 µM, 20 µM and 40 µM. The cells were then assessed for cell proliferation and survival using an MTT assay. FIG. 18 shows the results of the assays for A375 cells cultured in the presence of free curcumin, empty liposomes or liposomal curcumin for 72 hours, as a percentage of growth versus the control cells. FIG. 19 shows the results of the assays for HT-144 cells cultured in the presence of free curcumin, empty liposomes or liposomal curcumin for 96 hours, as a percentage of growth versus the control cells.

Example 7

Figure 20:
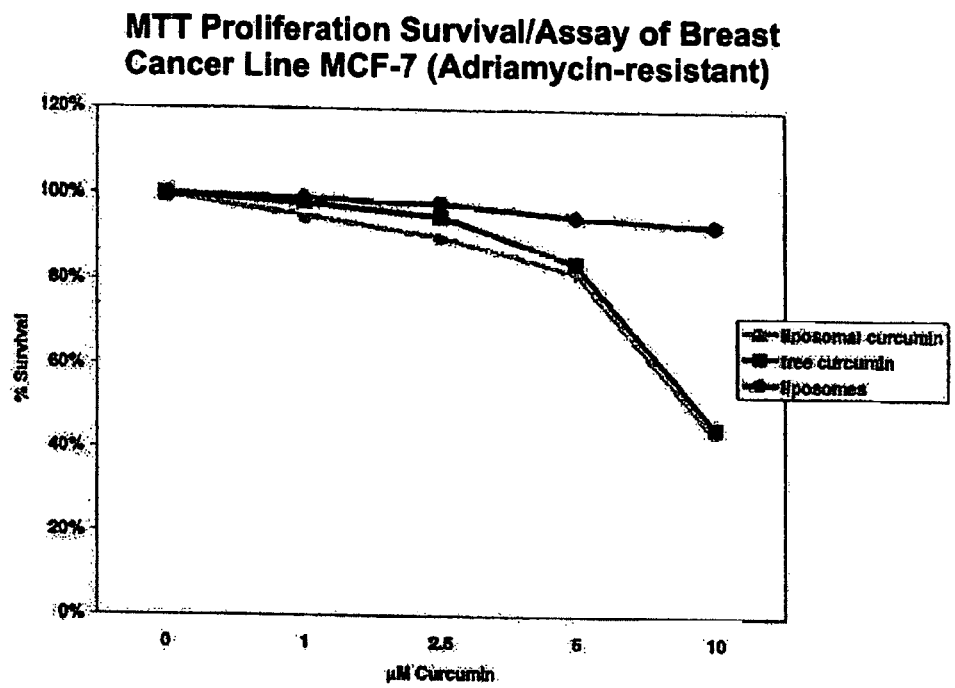
FIG. 20 MTT assay of the effects of liposomal curcumin on wild-type, Adriamycin-sensitive MCF-7 breast cancer cells.
Figure 21:
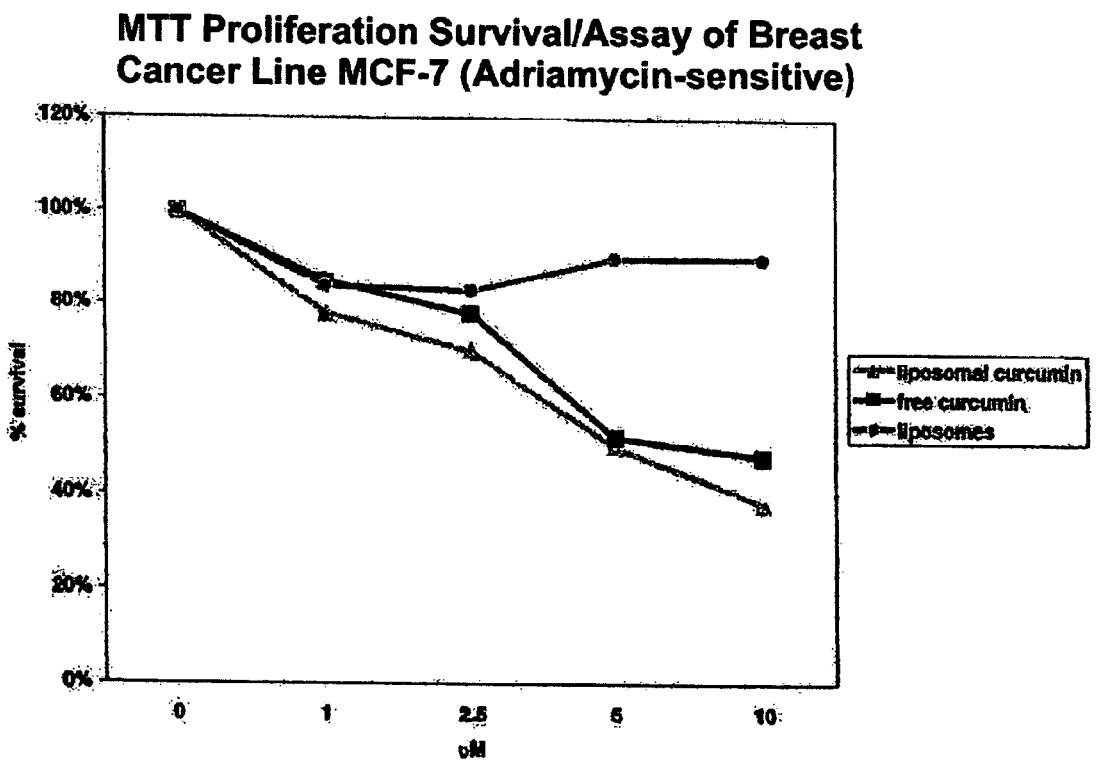
FIG. 21 MTT assay of the effects of liposomal curcumin on Adriamycin-resistant MCF-7 breast cancer cells.

Liposomal curcumin has anti-proliferative effects on breast cancer cells. Liposomal curcumin was shown to inhibit the proliferation of cells of the breast cancer cell line MCF-7. The effects of liposomal curcumin were compared to those of liposomes alone and to free curcumin. Two forms of MCF-7 breast cancer line were used—one resistant to Adriamycin and one which is sensitive to Adriamycin (wild type (wt)). MTT proliferation/survival assay was performed after 48 hours of incubation. The results, shown in FIGS. 20 and 21, demonstrate that liposomal curcumin inhibits both the Adriamycin-resistant and the sensitive line. Its effects are equivalent to those of free curcumin.

Example 8

The present invention can be used for the treatment of cancers. In particular, the present invention may be used for the treatment of pancreatic cancer.

To treat a human patient or other mammalian subject having pancreatic cancer an effective amount of curcumin or curcumin analogue encapsulated in a colloidal drug delivery system is administered parenterally to the animal or patient. Lower limits on the amount of therapeutic agent to be administered is the amount required to elicit a therapeutic effect as determined based upon animal pharmacology and early phase clinical trials in humans, both of which are standard activities and practices in the pharmaceutical industry. The upper limits on the amount of therapeutic agent to be administered is determined based on the toxicity of the therapeutic agent used. One of skill in the art could identify and quantify variables that would define the toxicity associated with the colloidal drug delivery system containing curcumin or curcumin analogue encapsulated curcumin or curcumin analogue.

Example 9

To treat a human patient or other mammalian subject having breast cancer an effective amount of curcumin or curcumin analogue encapsulated in a colloidal drug delivery system is administered parenterally to the animal or patient. Lower limits on the amount of therapeutic agent to be administered is the amount required to elicit a therapeutic effect as determined based upon animal pharmacology and early phase clinical trials in humans, both of which are standard activities and practices in the pharmaceutical industry. The upper limits on the amount of therapeutic agent to be administered is determined based on the toxicity of the therapeutic agent used. One of skill in the art could identify and quantify variables that would define the toxicity associated with the colloidal drug delivery system containing curcumin or curcumin analogue encapsulated curcumin or curcumin analogue.

Example 10

To treat a human patient or other mammalian subject having melanoma an effective amount of curcumin or curcumin analogue encapsulated in a colloidal drug delivery system is administered parenterally to the animal or patient. Lower limits on the amount of therapeutic agent to be administered is the amount required to elicit a therapeutic effect as determined based upon animal pharmacology and early phase clinical trials in humans, both of which are standard activities and practices in the pharmaceutical industry. The upper limits on the amount of therapeutic agent to be administered is determined based on the toxicity of the therapeutic agent used. One of skill in the art could identify and quantify variables that would define the toxicity associated with the colloidal drug delivery system containing curcumin or curcumin analogue encapsulated curcumin or curcumin analogue.

Example 11

The present invention can be used for the prevention of cancers. In particular embodiments, the present invention may be used for the prevention of pancreatic cancer, breast cancer or melanoma.

To serve as a cancer preventative or prophylactic, an effective amount of curcumin or curcumin analogue encapsulated in a colloidal drug delivery system is administered parenterally to the animal or human patient at risk for developing a specific cancer. Lower limits on the amount of therapeutic agent to be administered is the amount required to elicit a therapeutic effect as determined based upon animal pharmacology and early phase clinical trials in humans, both of which are standard activities and practices in the pharmaceutical industry. The upper limits on the amount of therapeutic agent to be administered is determined based on the toxicity of the therapeutic agent used. One of skill in the art could identify and quantify variables that would define the toxicity associated with the colloidal drug delivery system containing curcumin or curcumin analogue encapsulated curcumin or curcumin analogue.

Example 12

Conventional and sterically-stabilized (PEGylated) liposomes were studied for their efficiency of curcumin incorporation. The results are indicated in Table 2. The numbers in the composition and charge column represent the weight to weight (w/w) ratio of the respective lipids in the formulation in liposomes containing more than one type of lipid.

The curcumin encapsulation efficiency was determined after the liposomes were reconstituted with saline using a pipette to produce 10 µl of suspension. The suspension was checked by microscopy at 400× in both visible light and fluorescence light. "No" indicates that crystals and needles of free curcumin remained. "Yes" indicates no crystals and needles of free curcumin remained. Liposomes that could be reconstituted with saline at room temperature or by bath sonication at 37° C. for 5 to 10 minutes were classified "Yes" for ease of handling.

The tendency of the liposomal particles to self-aggregate was checked under a microscope after reconstitution in saline. "No" indicates that self-aggregation was not observed; "Yes" indicates that it was.

The data found in the growth inhibition column of Table 2 was generated using an MTT assay to assess growth and survival of tested cells. The pancreatic cancer cells Bxpc-3 were plated in 96-well plates overnight and 7.5 µg/ml of either free or liposomal curcumin was added and incubated for 72 hours. MTT dye (5 mg/ml in PBS) was added and incubated for 4 hours. At the end of the incubation, the amount of formazan formed was read at 570 nm and the results are as indicated.

Liposomal toxicity was also assessed. The pancreatic cancer cells Bxpc-3 were plated in 96-well plates overnight. Empty liposomes not containing curcumin were supplied in a quantity equivalent to that of the curcumin-containing liposomes used in the growth inhibition study. The empty liposomes were added to the Bxpc-3 cells and incubated for 72 hours. MT dye (5 mg/ml in PBS) was added and incubated for 4 hours and at the end of incubation, the amount of the formazan formed was read at 570 nm. The results are as indicated in the column labeled "liposome toxicity."

In Table II, "PC" denotes L-α-phosphatidylcholine (egg, chicken) and "PS" denotes L-α-phosphatidylserine (brain, porcine)(sodium salt).

TABLE II

Summary of characteristics of various liposomal-curcumin formulations.

| Composition and charge w/w | Curcumin encapsulates efficiency | Ease of Handling | Liposome self Aggregation | Growth Inhibition | Liposome Toxicity |
|---|---|---|---|---|---|
| Conventional Liposome Neutral | | | | | |
| PC | Low | | | | |
| PC:chol 9:1 | Low | | | | |
| PC:chol 7:3 | Low | | | | |
| DMPC | High | Yes | Yes | 79 ± 1.6 | 13 |
| DMPC:Chol 9:1 | High | Yes | Yes | 89 ± 0.1 | 17 |

TABLE II-continued

Summary of characteristics of various liposomal-curcumin formulations.

| Composition and charge w/w | Curcumin encapsulates efficiency | Ease of Handling | Liposome self Aggregation | Growth Inhibition | Liposome Toxicity |
|---|---|---|---|---|---|
| DOPC | Low | | | | |
| DPPC | High | No | | | |
| DPPC:Chol (90:11.5) | High | No | Yes | | |
| Positively charged | | | | | |
| DMPC:SA 9:1 | Low | | | | |
| Negatively charged | | | | | |
| DMPC:DMPG 7:3 | Low | | | | |
| DMPC:DMPG 9:1 | High | Yes | No | 81 ± 4 | 11 |
| DMPC:Chol:DMPG 8:1:1 | High | Yes | Yes | 65 ± 0.4 | 17 |
| DPPC:DMPG 7:3 | Low | | | | |
| DPPC:DMPG 9:1 | High | No | No | 81 ± 4 | 14 |
| DPPC:Chol:DMPG 8:1:1 | High | No | Yes | 67 ± 0.06 | 14 |
| DPPC:DPPG 7:3 | Low | | | | |
| DOPC:DMPG 7:3 | Low | | | | |
| DOPC:DMPG 9:1 | Low | | | | |
| PC:PS:Chol 7:3:1 | Low | | | | |
| Sterically-Stabilized | | | | | |
| Liposome | | | | | |
| Pegylated and | | | | | |
| Negatively charge | | | | | |
| DMPC:DMPE-PEG-2000 90:10 | Low | | | | |
| DMPC:DMPE-PEG-2000 95:5 | High | Yes | No | 58.5 ± 4.5 | 22.5 |
| DMPC:DMPE-PEG-2000 97:3 | Low | | | | |
| DMPC:Chol:DMPE-PEG-2000 90:10:05 | High | Yes | No | 85 ± 1 | 13.5 |
| DMPC:DSPE-PEG-2000 95:5 | High | No | No | 64 ± 4 | 20 |
| DMPC:Chol:DSPE-PEG-2000 90:10:05 | High | No | No | 69 ± 9 | 19 |

As shown by the results of Table 2, the optimal formulations of liposomal curcumin included DMPC/DMPG (9:1) and DMPC/CHOL/DMPE-PEG-2000 (90:10:5). The latter is a pegylated formulation. These formulations were chosen as being optimal among the compositions studied on the basis of their properties including (i). encapsulation efficiency, (ii) ease of handling, (iii) liposome self-aggregation, (iv) growth inhibition and (v) level of toxicity of empty liposomes.

Example 13

The optimal curcumin-to-lipid ratio (weight-to weight) was determined for several liposomal curcumin formulations made using DMPC. The ease of handling was determined by determining whether or not the lipid-curcumin mixture could be readily dissolved in t-butanol without DMSO. Although DMSO had been used in previous studies, t-butanol may be preferred for certain pharmaceutical uses. The degree to which free curcumin associated with the lipid without the formation of needles or crystals of free curcumin was assessed by microscopy. The optimal curcumin-to-DMPC ratio among the ratios tested was 1:10.

TABLE III

Optimization of the Curcumin-to-Lipid ratio in Liposomal Curcumin Formulations

| Curcumin:DMPC (w/w) | Ease of Handling | Curcumin:Lipid Association |
|---|---|---|
| 1:10 | Yes | Curcumin completely associated with liposome |
| 1:7.5 | Yes | Very few curcumin crystals |
| 1:5 | No | Few curcumin crystals |

Example 14

A variety of lipids and lipid mixtures were assayed for their ability to form liposomes encapsulating curcumin and the results are disclosed in Table IV. The t-butanol was pre-warmed for 10 min at 37° C. Lipids were weighed out in the appropriate quantities and placed in glass vials and 25 ml of pre-warmed t-butanol is added to each vial. The mixtures were vortexed and sonicated in a bath sonicator (Branson 2200, Danbury, Conn.) for 5 min. The curcumin was weighed out and 5 mg of curcumin was added to each vial. The mixtures were vortexed in the sonicator bath for 5 min. until the curcumin was completely dissolved. The vials were frozen in a dry ice-acetone bath and lyophilized for 24 hours in a Freeze Dry System (Freezone 4.5, Labconco). The vials were stored at −20° C. in a container that protected the composition from exposure to light. The lyophilized powder was subsequently warmed to room temperature for 10 min. and reconstituted with saline (0.9% NaCl) at 4 mg/ml using a bath sonicator for 5 min. From each vial, 10 µl of each formulation was placed on a glass slide, covered with a cover slide and checked for appearance under a fluorescence microscope.

The numbers after the abbreviations in the Lipid Composition column of Tables IV and V indicate the proportions of lipids used in the lipid mixtures; ratios in brackets are lipid to curcumin ratios (w/w). Table IV notes the appearance of the lyophilizate for each formulation, the ease of the reconstitution in saline and the appearance of the reconstituted composition under a microscope. The reconstituted liposomes were centrifuged at 1000 rpm for 10 minutes, and the appearance of the pellet and supernatant was noted. Free curcumin and larger liposomes will tend to accumulate in the pellet. Experimental observations are listed in the final column of Table IV. "SA" denotes stearylamine. In Table IV, "PC" denotes L-α-phosphatidylcholine (egg, chicken) and "PS" denotes L-α-phosphatidylserine (brain, porcine)(sodium salt). As used herein, any characterization that a formulation was "poor" or that it performed "poorly" in a particular application is not an indication that the formulation is unsuitable for use, but merely reflects that the formulation was less preferred than other formulations under the assay conditions tested.

TABLE IV

Encapsulation Efficiency of Various Conventional Liposomal Curcumin Formulations
Part I

| Lipid Composition | Appearance after Lyophilization | Ease of Reconstitution | Appearance after Centrifugation | Comments |
| --- | --- | --- | --- | --- |
| DMPC/DMPG 7:3 | Fluffy powder | Easy to reconstitute; very few crystals and needles; adequate liposomes | Small pellets; unclear supernatant | Curcumin is encapsulated well |
| PC/PS/Chol 7:3:1 | Unevenly distributed film | Easy to reconstitute; crystals and needles are present | Small pellets; unclear supernatant | Curcumin is encapsulated poorly |
| DMPC/SA 9:1 | Red cake | On addition of SA to the solution it turned red and formed a solid-colored cake | Dark orange color pellets | Unacceptable; a chemical reaction between SA and curcumin appears to have occurred |
| DPPC | Fluffy powder | Hard to reconstitute; | Quite clear supernatant Uniform pellets | Difficult to handle |
| DPPC/DPPG | Fluffy powder | Hard to reconstitute; few crystals and needles | Small pellets; unclear supernatant | Difficult to handle |
| DPPC/DMPG 7:3 | Fluffy powder | few crystal and needles | Small pellets; unclear supernatant | Curcumin is encapsulated well |
| DOPC/DMPG 7:3 | Unevenly distributed film | Easy to reconstitute; few crystal and needles | Small pellets; unclear supernatant | Curcumin is encapsulated poorly |
| DMPC [10:1] | Fluffy powder | Nice liposomes | Quite clear supernatant; uniform pellets | Optimal curcumin encapsulation |
| DMPC [7.5:1] | Fluffy powder | Nice liposomes and very few crystals | Quite clear supernatant; uniform pellets | Curcumin is encapsulated poorly |
| DMPC [5:1] | Fluffy powder | Nice liposomes and few crystals | Quite clear supernatant; uniform pellets | Curcumin is encapsulated poorly |
| DOPC [10:1] | Evenly distributed film | Easy to reconstitute; few crystals and needles | Quite clear supernatant; uniform pellets | Optimal curcumin encapsulation |
| DOPC [7.5:1] | Evenly distributed film | Easy to reconstitute; crystals and needles | Quite clear supernatant; uniform pellets | Curcumin is encapsulated poorly |
| DOPC [5:1] | Evenly distributed film | Easy to reconstitute; many crystals and needles | Quite clear supernatant; uniform pellets | Curcumin is encapsulated poorly |
| PC | Unevenly distributed film | Uneven-sized, self-aggregated liposomes; crystals | Quite clear supernatant; uniform pellets | Curcumin is encapsulated poorly |
| PC/Cholesterol 9:1 | Unevenly distributed film | Uneven-sized, self-aggregated liposomes; crystals | Quite clear supernatant; uniform pellets | Curcumin is encapsulated poorly |
| PC/Cholesterol 7:3 | Unevenly distributed film | Uneven-sized, self-aggregated liposomes; crystals | Quite clear supernatant; uniform pellets | Curcumin is encapsulated poorly |

Table V lists the observed encapsulation properties of several other lipid compositions. The comments indicate the optimal and preferred liposomal compositions among those tested. The protocol used to obtain the data in Table V is as follows:

Material:
DMPC; DPPC, DMPG, DOPC, PC, Cholesterol (Avanti Polar Lipids, Alabaster, Ala. 35007)
T-butanol (Sigma)
Dry ice
Acetone (Sigma)
Heat-resistant glass vial
Curcumin (Sigma)

Equipment:
1. Freeze Dry System (Labconco, Fisher Scientific)
2. Sonicator (Branson 2200, Danbury, Conn.)

Method:
1. Pre-warm T-butanol for 10 min. at 37° C.
2. Weigh out DPPC: 45 mg and DMPG 5 mg (9:1); DMPC 50 mg; DOPC: 50 mg; PC 45 mg and Cholesterol 5 mg (9:1); DMPC 45 mg and DMPG 5 mg (9:1); DOPC 45 mg and DMPG 5 mg (9:1), and put into 6 glass vials.
3. Add 25 ml pre-warmed T-butanol to each vial. Vortex and sonicate at a bath sonicator for 5 min.
4. Weigh out curcumin 6×5 mg (5 mg/vial) add to each vial above vortex and bath sonicate for 5 min until curcumin completely dissolved.
5. Aliquot and freeze vials at a Dry ice-acetone bath and lyophilize for 24 hours at a Freeze Dry System (Freezone 4.5, Labconco). Store at −20° C.
6. Warm up the liposomal curcumin powder at room temperature for 10 min. Reconstitute with saline (0.9% NaCl) at 4 mg/ml, bath sonicate for 5 min.
7. Take 10 µl of each formulation vial and put on a glass slide and covered with a cover slide and check under a fluorescence microscope.
8. Powder is stored in a container that protects it from exposure to light.

The results are as follows:

TABLE V

Encapsulation Efficiency of Various Conventional Liposomal Curcumin Formulations Part II

| Lipid Composition | Appearance after Lyophilization | Ease of Reconstitution | Appearance after Centrifugation | Comment |
|---|---|---|---|---|
| DPPC/DMPG 9:1 | Nice fluffy powder | Hard to reconstitute with saline; very nice liposomes | Large volume of yellow precipitations (L-cur), Very small volume of orange-colored precipitate (Free curcumin). | GOOD |
| DMPC | Nice fluffy powder | Easy to reconstitute with saline at 37° C.; very nice liposomes | Large volume of yellow precipitations (L-cur), Very small volume of orange-colored precipitate (Free curcumin). | GOOD |
| DOPC | Unevenly distributed film | Easy to reconstitute with saline at room temperature; needles and crystals present | Small volume of yellow precipitations (L-cur), Large volume of orange-colored precipitate (Free curcumin). | POOR |
| PC/Cholesterol 9:1 | Unevenly distributed film | Easy to reconstitute with saline; needles and crystals present | Small volume of yellow precipitations (L-cur), Large volume of orange-colored precipitate (Free curcumin). | POOR |
| DMPC/DMPG 9:1 | Nice fluffy powder | Easy to reconstitute with saline at 37° C.; very nice liposomes | Very large volume of yellow precipitations (L-cur), trace of orange-colored precipitate (Free curcumin). | OPTIMAL |
| DOPC/DMPG 9:1 | Unevenly distributed film | Easy to reconstitute with saline at room temperature; needles and crystals present | Small volume of yellow precipitations (L-cur), Large volume of orange-colored precipitate (Free curcumin). | POOR |

Example 15

Several preferred formulations of pegylated liposomes where prepared and tested according to the following protocol:

Material:
- DMPC; DMPE peg 2000; (Avanti Polar Lipids, Alabaster, Ala. 35007)
- T-butanol (Sigma)
- Dry ice
- Acetone (Sigma)
- Heat-resistant glass vial
- 6: Curcumin (Sigma)

Equipment:
- 3. Freeze Dry System (Labconco, Fisher)
- 4. Sonicator (Branson 2200, Danbury, Conn.)

Method:
1. Pre-warm T-butanol for 10 min. at 37° C.
2. Weigh out DMPC 45 mg and DMPE peg 2000 5 mg (90:10); DMPC 47.5 mg and DMPE peg 2000 2.5 mg (95:5); DMPC 48.5 mg and DMPE peg 2000 1.5 mg (97:3), and put into 3 glass vials.
3. Add 25 ml pre-warmed t-butanol to each vial. Vortex and sonicate in a bath sonicator for 5 min.
4. Weigh out curcumin 3×5 mg (5 mg/vial) ads to each vial above vortex and bath sonicate for 5 min until curcumin completely dissolved.
5. Aliquot and freeze vials at a Dry ice-acetone bath and lyophilize for 24 hours at a Freeze Dry System (Freezone 4.5, Labconco). Store at −20° C.
6. Warm up the Liposomal Curcumin powder at room temperature for 10 min. Reconstitute with saline (0.9% NaCl) at 4 mg/ml, bath sonicate for 5 min.
7. Take 10 µl of each formulation vial and put on a glass slide and covered with a cover slide and check under a fluorescence microscope.
8. Powder is stored in a container that protects it from exposure to light.

The formulations were reconstituted and checked by microscopy, as above. The formulations were assessed for ease of handling, reconstitution and encapsulation characteristics as in the examples above. The results are shown in Table VI and VII. Among the formulations tested in Table VI, DMPC:DMPE-PEG-2000 95:5 (w/w) was found to have optimal properties. As used herein, any characterization that a formulation was "poor" or that it performed "poorly" in a particular application is not an indication that the formulation is unsuitable for use, but merely reflects that the formulation was less preferred than other formulations under the assay conditions tested.

TABLE VI

Optimization of Lipid/PEGylated Lipid Ratios in Liposomal Curcumin Formulations

| DMPC:DMPE PEG-2000 (w/w) | Ease of Handling | Ease of Reconstitution | Curcumin encapsulation efficiency | Comments |
| --- | --- | --- | --- | --- |
| 90:10 | Yes | Liposomes present; uneven size particles; crystals and needles present | ++ | POOR |
| 95:5 | Yes | Nice liposomes; uneven size particles; very few crystals | ++++ | OPTIMAL |
| 97:3 | Yes | Liposomes present; uneven size particles; a few crystals and a few self-aggregated liposomes | ++++ | GOOD |

Of the formulations tested in Table VII, the optimal formulation was DMPC/Cholesterol/DMPE-PEG-2000, 90:10:5 (w/w). The liposomes did not appear to self-aggregate and tended to remained in suspension during centrifugation. Very little free curcumin was observed in this formulation.

TABLE VII

Encapsulation Efficiency of Various Sterically-Stabilized (PEGylated) Liposomal Curcumin Formulations

| Lipid composition | Ease of Handling | Ease of Reconstitution | Appearance after centrifugation | Comments |
| --- | --- | --- | --- | --- |
| DMPC/Chol 9:1 (w/w) | Yes | Nice liposome; even size particles; self-aggregated liposomes | Nice pellets; clear supernatant; some free cucumin observed | POOR, liposomes self-aggregate |
| DMPC/Chol/ DMPE-PEG-2000 90:10:5 (w/w) | Yes | Nice liposomes, easy to handle; uneven size particles | Liposomes remain suspended; small pellets; very little free curcumin observed | OPTIMAL |

TABLE VII-continued

Encapsulation Efficiency of Various Sterically-Stabilized (PEGylated) Liposomal Curcumin Formulations

| Lipid composition | Ease of Handling | Ease of Reconstitution | Appearance after centrifugation | Comments |
|---|---|---|---|---|
| DMPC/Chol/ DSPE-PEG-2000 90:10:5 (w/w) | No | Nice liposomes, easy to handle; uneven size particles | Liposomes remain suspended; small pellets; some free curcumin observed | GOOD |
| DMPC/DMPE-PEG-2000 95:5 (w/w) | Yes | Nice liposomes, easy to handle; uneven size particles | Liposomes remain suspended; small pellets; very little free curcumin observed | GOOD, but empty liposomes are toxic to Miapaca-2 cells |
| DMPC/DSPE-PEG-2000 95:5 (w/w) | No | Nice liposomes, easy to handle; uneven size particles | Liposomes remain suspended; small pellets; very little free curcumin observed | GOOD, but empty liposomes are toxic to Miapaca-2 cells |

Example 16

Figure 22:
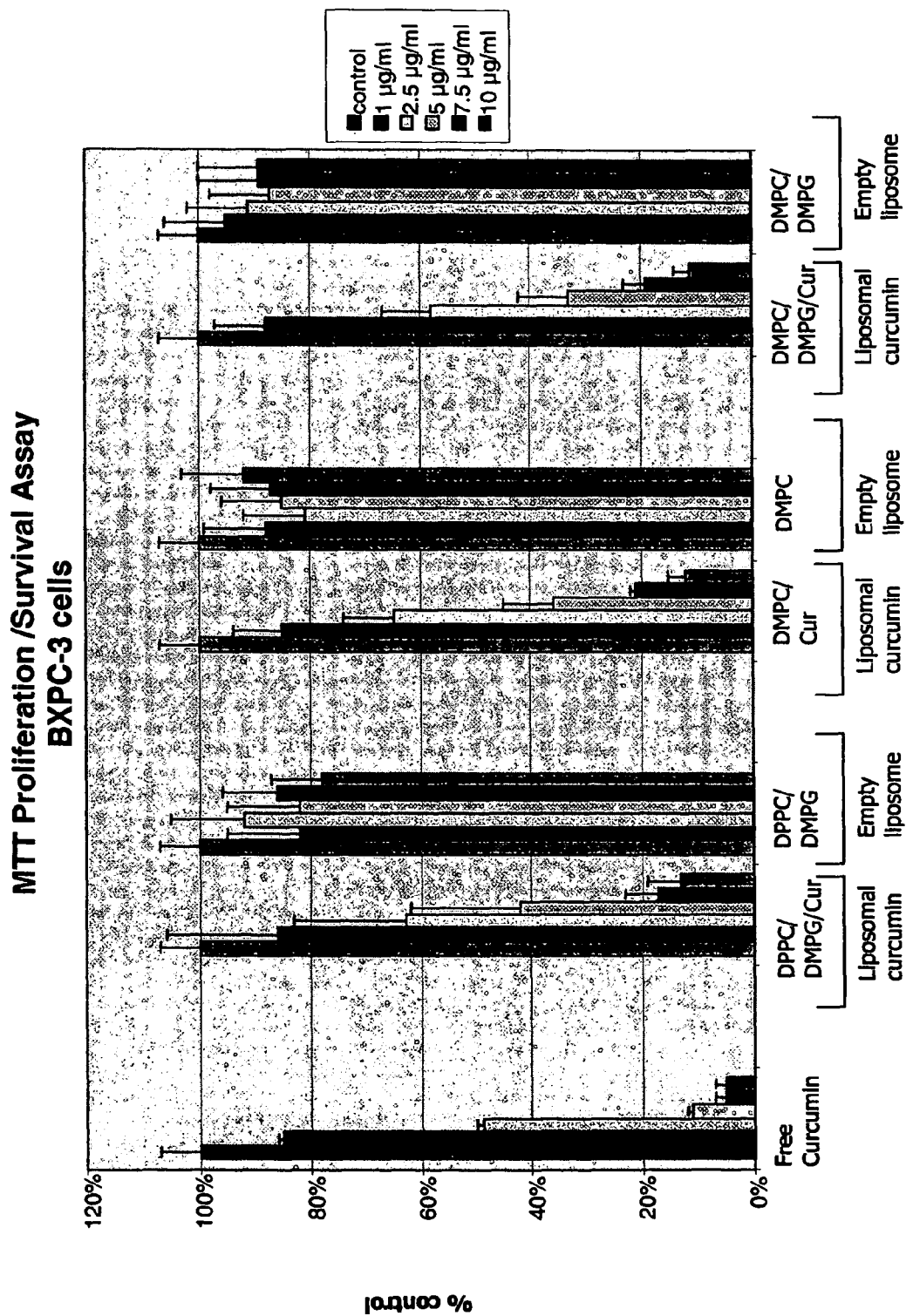
FIG. 22 MTT proliferation and survival assay of the effects of liposomal curcumin on BXPC-3 cells.
Figure 23:
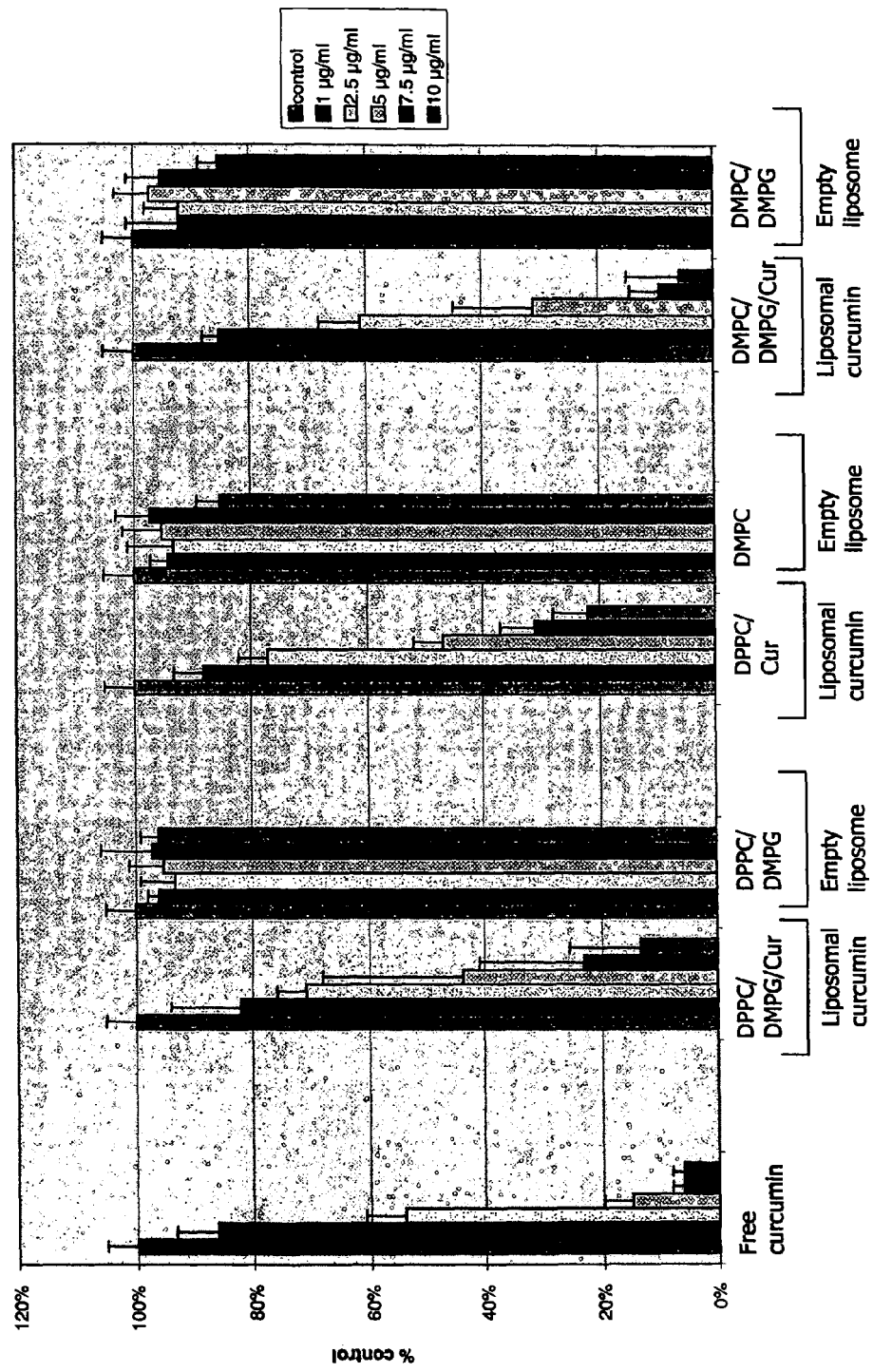
FIG. 23 MTT proliferation and survival assay of the effects of liposomal curcumin on MiaPaCa-2 cells.
Figure 24:
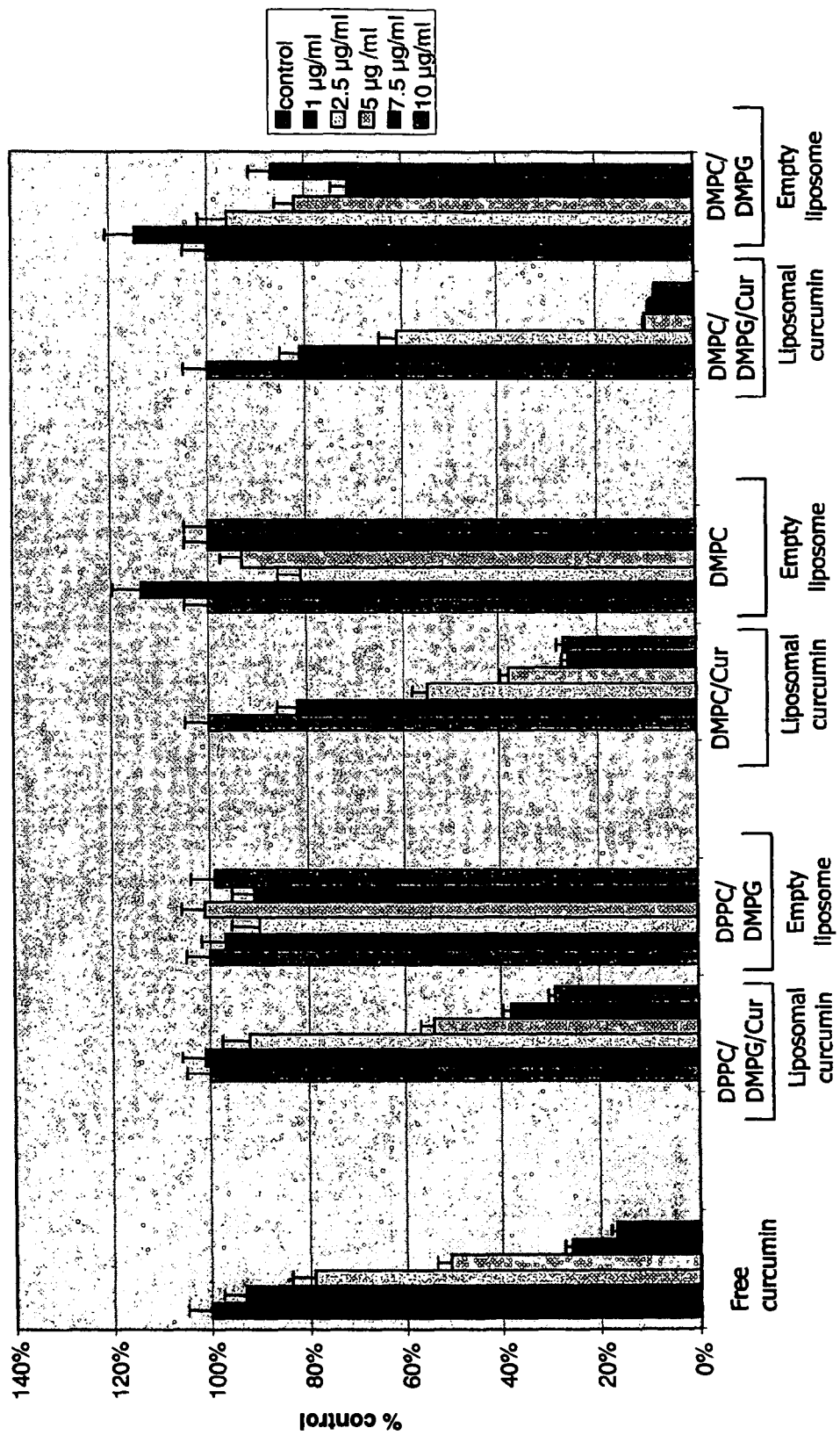
FIG. 24 MTT proliferation and survival assay of the effects of liposomal curcumin on ASPC-1 cells.

Various conventional liposomal curcumin formulations were tested for their effects on cancer cell proliferation and survival using the MTT assay described in previous examples. FIGS. 22-24 compare the effects of liposomal curcumin and empty liposomes on the growth of several strains of human pancreatic cancer cells. FIG. 22 assesses BXPC-3 cells, FIG. 23 assesses MiaPaCa-2 cells, and FIG. 24 assesses ASPC-1 cells.

In FIGS. 22-24, DPPC/DMPG and DPPC/DMPG/Cur have lipid ratios of 9:1 and the liposomal curcumin formulation has a lipid to curcumin ratio of 10:1. The liposomes were prepared by the following protocol:

All curcumin-containing formulations have a lipid to curcumin ratio of 10:1. The DPPC/DMPG and DMPC/DMPG formulations have lipid ratios of 9:1. The liposomes were prepared by the following protocol:

Material:
DPPC; DMPG; DMPC; (Avanti Polar Lipids, Alabaster, Ala. 35007)
T-butanol (Sigma)
Dry ice
Acetone (Sigma)
Heat-resistant glass vial
Curcumin (Sigma)

Equipment:
1. Freeze Dry System (Labconco, Fisher)
2. Sonicator (Branson 2200, Danbury, Conn.)

Method:
Pre-wann T-butanol for 10 min. at 37° C.
1. Weigh out appropriate quantities of lipid to achieve the indicated lipid ratios for a total of 50 mg of lipid, and put into 5 glass vials.
2. Add 25 ml pre-warmed T-butanol to each vial. Vortex and sonicate in a bath sonicator for 5 min.
3. Weigh out curcumin 5×5 mg (5 mg/vial) add to each vial above vortex and bath sonicate for 5 min until curcumin completely dissolved.
4. Aliquot and freeze vials at a Dry ice-acetone bath and lyophilize for 24 hours at a Freeze Dry System (Freezone 4.5, Labconco). Store at −20° C.
5. Warm up the Liposomal Curcumin powder at room temperature for 10 min. Reconstitute with saline (0.9% NaCl) at 4 mg/ml, bath sonicate for 5 min.
6. Take 10 μl of each formulation vial and put on a glass slide and covered with a cover slide and check under a fluorescence microscope.
7. Powder is stored in a container that protects it from exposure to light.

For each figure, the pancreatic cancer cells were grown in 96-well plates overnight. Free curcumin and liposomal curcumin was added to the media at concentrations ranging from 1 to 10 μl/ml. Empty liposomes were added at concentrations equivalent to the lipid concentration found in the liposomal curcumin formulations. The cells were incubated for 72 hours after the addition of free curcumin or liposomes and then cell viability was assessed using the MTT assay. The results shown by the bars are the mean values for three different experiments. The error bars indicate the standard deviation for each set of experiments.

Example 17

Figure 25:
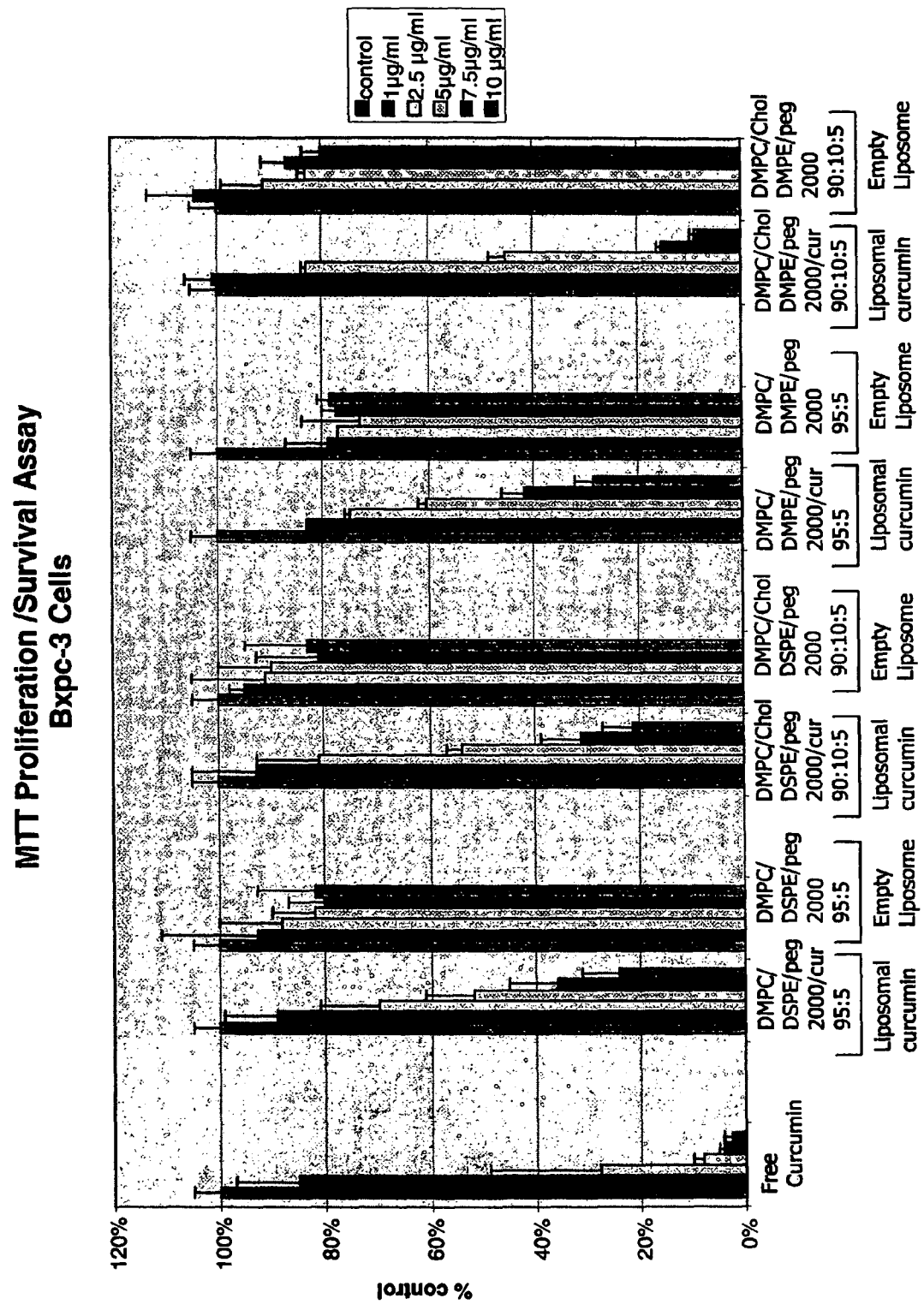
FIG. 25 MTT proliferation and survival assay of the effects of liposomal curcumin on BXPC-3 cells.
Figure 26:
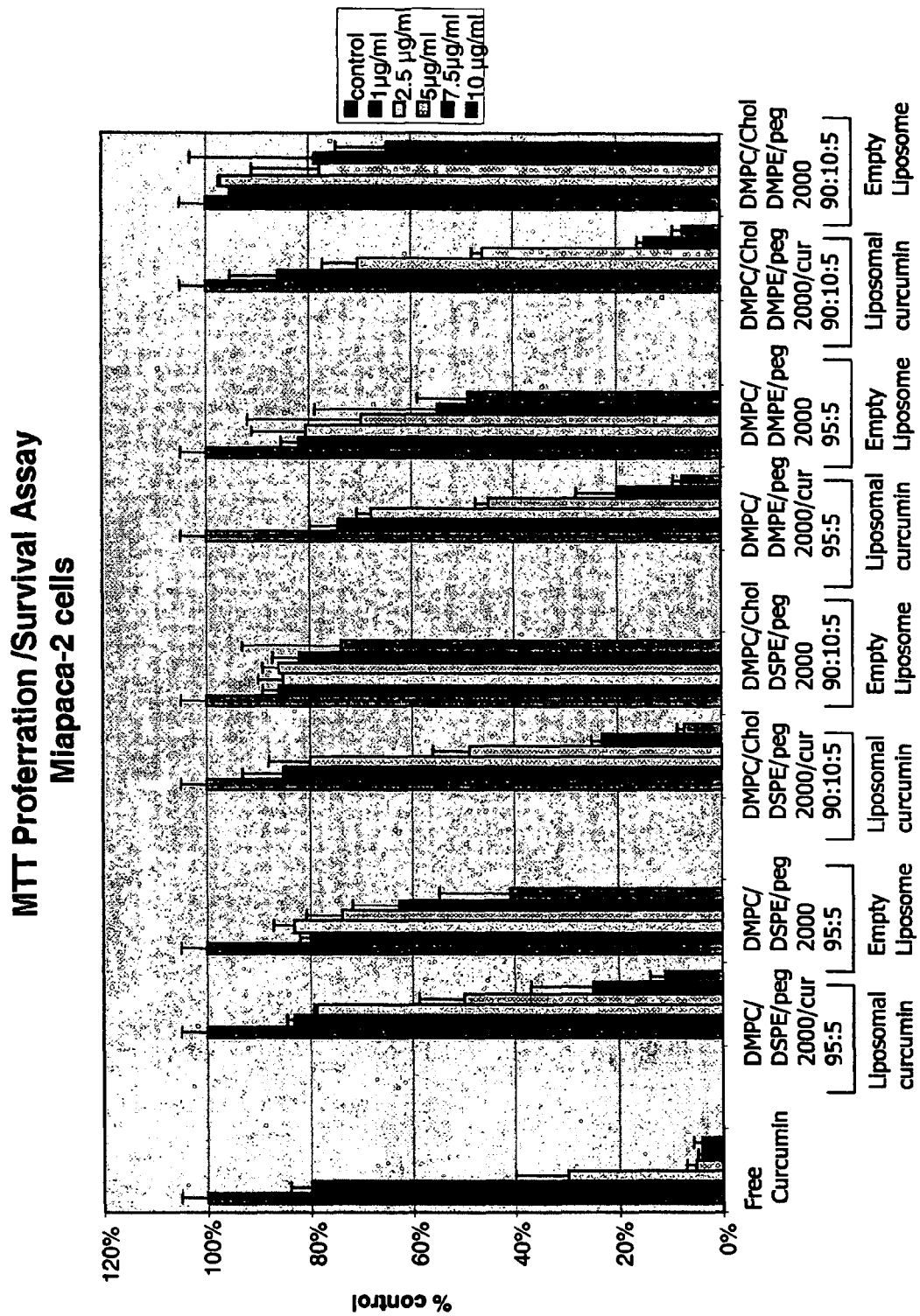
FIG. 26 MTT proliferation and survival assay of the effects of liposomal curcumin on MiaPaCa-2 cells.

Various PEGylated liposomal curcumin formulations were tested for their effects on cancer cell proliferation and survival using the MTT assay described in previous examples. FIGS. 25 and 26 compare the effects of liposomal curcumin and empty liposomes on the growth of two strains of human pancreatic cancer cells. FIG. 25 assesses BXPC-3 cells and FIG. 26 assesses MiaPaCa-2 cells.

In FIGS. 25 and 26, liposomes containing curcumin contain a lipid to curcumin ratio of 10:1. The liposomes were prepared by the same protocol as in Example 16 except that the lipids used included DMPE-PEG-2000; DSPE-PEG-2000 and Cholesterol from Avanti Polar Lipids, Alabaster, Ala. 35007.

For each figure, the pancreatic cancer cells were grown in 96-well plates overnight. Free curcumin and liposomal curcumin was added to the media at concentrations ranging from 1 to 10 μg/ml. Empty liposomes were added at concentrations equivalent to the lipid concentration found in the liposomal curcumin formulations. The cells were incubated for 72 hours after the addition of free curcumin or liposomes and then cell viability was assessed using the MTT assay. The results shown by the bars are the mean values for three different experiments. The error bars indicate the standard deviation for each set of experiments.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept, spirit and scope of the invention. More specifically, it will be apparent that certain agents that are chemically or physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

Allen and Choun, *FEBS Lett.*, 223:42-46, 1987.
Araújo and Leon, Mem. Inst. Oswaldo Cruz, 96:723, 2001.
Couvreur et al., *FEBS Lett.*, 84:323-326, 1977.
Couvreur et al., U.S. patent 4:489-555, 1984.
Couvreur, *Crit. Rev. Ther. Drug Carrier Syst.*, 5:1-20, 1988.
Couvreur et al., *Pharm. Res.*, 8:1079-1086, 1991.
Desiderio and Campbell, *J. Reticuloendothel. Soc.*, 34:279-287, 1983.
Düzgünes et al., *Antimicrob. Agents Chemother.*, 32:1404-1411, 1988.
Fattal et al., *Antimicrob. Agents Chemother.*, 33:1540-1543, 1989.
Fattal et. al., *J Microencapsul*, 8(1):29-36, 1991a.
Fattal et. al., *Antimicrob Agents Chemother*, 35(4):770-772, 1991b.
Fountain et al, *J. Infect Dis.*, 152-529-535, 1985.
Gabizon and Papahadjopoulos, *Proc. Natl. Acad. Sci. USA*, 85:6949-6953, 1988.
Grislain et al., *Int. J. Pharm.*, 15:335-345, 1983.
Henry-Michelland et al., *Int. J. Pharm.*, 35:121-127, 1987.
Ireson, C., *Cancer Research* 61:1058-64, 2001
John et al., *J. Exp. Clin. Cancer Res.*, 21:219-24, 2002.
Lin et al., Cancer Lett. 168:125, 2001.
Mastrobattista et al., Advanced Drug Delivery Reviews, 40:103-180.
Mosman T, J. Immunol. Methods, 65:55, 1983.
Poste, *Biol. Cell.*, 47:19-39, 1983.
Tulkens, In P. Buri and R. Gumma (eds.), *aims, Potentialities and Problems in Drug Targeting*, Elsevier, Amsterdam, 1985, pp. 179-194.
Woodle et al., Pharmaceutical Research 9, 260-265 (1992)

What is claimed is:

1. A method for inhibiting the growth of melanoma, pancreatic and breast carcinoma cells, comprising:
exposing said cells in vitro to formulation of a liposomal drug delivery system encapsulating at least one of a curcumin, wherein the ratio of curcumin to a lipid combination (weight to weight) is 1:7.5 to 1:10, wherein the lipid combination is selected from: DMPC; DMPC:Chol 9:1; DMPC:DMPG 9:1; DMPC:Chol:DMPG 8:1:1; DPPC:DMPG 9:1; DPPC:Chol:DMPG 8:1:1; DMPC:DSPE-PEG-2000 95:5; DMPC:Chol:DSPE-PEG-2000 90:10:05; DMPC/DMPG 7:3; DPPC/DMPG 7:3; DPPC/DMPG 9:1
wherein the formulation is capable of inhibiting the said cells.

2. The method of claim 1, wherein the cells are from is a human cancer patient.

3. A composition that inhibits the growth of melanoma, pancreatic and breast carcinoma cell lines in vitro comprising a curcumin, encapsulated in a liposomal drug delivery system wherein the weight to weight ratio of curcumin to a lipid combination is 1:7.5 to 1:10, wherein the lipid combination is selected from: DMPC; DMPC:Chol 9:1; DMPC:DMPG 9:1; DMPC:Chol:DMPG 8:1:1; DPPC:DMPG 9:1; DPPC:Chol:DMPG 8:1:1; DMPC:DSPE-PEG-2000 95:5; DMPC:Chol:DSPE-PEG-2000 90:10:05; DMPC/DMPG 7:3; DPPC/DMPG 7:3; DPPC/DMPG 9:1.

* * * * *